United States Patent [19]

Lamarco et al.

[11] Patent Number: 5,453,362
[45] Date of Patent: Sep. 26, 1995

[54] EUKARYOTIC TRANSCRIPTION PROTEIN; HOST CELL FACTOR

[75] Inventors: Kelly Lamarco, San Francisco, Calif.; Angus Wilson, Cold Spring Harbor; Winship Herr, Oyster Bay Cove, both of N.Y.

[73] Assignees: Tularik Inc., San Francisco, Calif.; Cold Spring Harbor Laboratory, Cold Spring Harbor, N.Y.

[21] Appl. No.: 46,585

[22] Filed: Apr. 12, 1993

Related U.S. Application Data

[63] Continuation-in-part of Ser. No. 989,842, Dec. 4, 1992, abandoned.

[51] Int. Cl.$^6$ ............................ C12N 15/12; C07H 21/04
[52] U.S. Cl. .................. 435/69.1; 435/6; 435/240.1; 435/252.3; 435/320.1; 536/23.5; 436/501; 530/350; 530/827
[58] Field of Search ................... 530/350, 358; 536/23.5; 435/69.1, 320.1

[56] References Cited

U.S. PATENT DOCUMENTS 4,399,216  8/1983  Axel ............................................. 435/6

OTHER PUBLICATIONS

A. D. Friedman et al. Nature 335(6189):452–4 Sep. 29, 1988.
Wozney, J. Meth. Enz. 182:738–751, 1990.
Matsudaira, P. MethEnz. 182:602–613, 1990.
S. Stern & W. Herr, Genes Dev. 5:2555–66, 1991.
M. Katan et al., Nucleic Acids Res. 18(23):6871–80, 1990.
T. M. Kristie & P. A. Sharp, Genes Dev. 4:2383–96, 1990.
P. Xiao & J. P. Capone, Mol. Cell. Biol. 10(9) 4974–7, Sep. 1990.

*Primary Examiner*—Garnette D. Draper
*Assistant Examiner*—Lorraine M. Spector
*Attorney, Agent, or Firm*—Flehr, Hohbach, Test, Albritton & Herbert

[57] ABSTRACT

Host Cell Factor (HCF), a eukaryotic cellular protein involved in transcription, nucleic acids encoding HCF, and methods of using HCF and HCF-encoding nucleic acids are provided. HCF activity is disclosed to comprise a collection of polypeptides encoded by a structural gene encoding a parent protein of 2039 amino acids. HCF-specific binding compounds are disclose including antibodies to HCF epitopes. Because HCF is required for the transcription of a number of vital genes such as the immediate early genes of Herpes Simplex Virus, the invention provides HCF-based methods for screening chemical libraries for regulators of viral transcription. Such regulators are used in the treatment of viral infections by modulating the transcription of certain viral genes.

4 Claims, 13 Drawing Sheets

Amino Acid Sequence of HCF

```
MASAVSPANLPAVLLQPRWKRVVGWSGPVPRPRHGHRAVAIKELIVVFGGGNEGIVDELH      60
VYNTATNQWFIPAVRGDIPPGCAAYGFVCDGTRLLVFGGMVEYGKYSNDLYELQASRWEW     120
KRLKAKTPKNGPPPCPRLGHSFSLVGNKCYLFGGLANDSEDPKNNIPRYLNDLYILELRP     180
GSGVVAWDIPITYGVLPPPRESHTAVVYTEKDNKKSKLVIYGGMSGCRLGDLWTLDIDTL     240
TWNKPSLSGVAPLPRSLHSATTIGNKMYVFGGWVPLVMDDVKVATHEKEWKCTNTLACLN     300
LDTMAWETILMDTLEDNIPRARAGHCAVAINTRLYIWSGRDGYRKAWNNQVCCKDLWYLE     360
TEKPPPPARVQLVRANTNSLEVSWGAVATADSYLLQLQKYDIPATAATATSPTPNPVPSV     420
PANPPKSPAPAAAAPAVQPLTQVGITLLPQAAPAPPTTTTIQVLPTVPGSSISVPTAART     480
QGVPAVLKVTGPQATTGTPLVTMRPASQAGKAPVTVTSLPAGVRMVVPTQSAQGTVIGSS     540
PQMSGMAALAAAAAATQKIPPSSAPTVLSVPAGTTIVKTMAVTPGTTTLPATVKVASSPV     600
MVSNPATRMLKTAAAQVGTSVSSATNTSTRPIITVHKSGTVTVAQQAQVVTTVVGGVTKT     660
ITLVKSPISVPGGSALISNLGKVMSVVQTKPVQTSAVTGQASTGPVTQIIQTKGPLPAGT     720
ILKLVTSADGKPTTIITTTQASGAGTKPTILGISSVSPSTTKPGTTTIIKTIPMSAIITQ     780
AGATGVTSSPGIKSPITIITTKVMTSGTGAPAKIITAVPKIATGHGQQGVTQVVLKGAPG     840
QPGTILRTVPMGGVRLVTPVTVSAVKPAVTTLVVKGTTGVTTLGTVTGTVSTSLAGAGGH     900
STSASLATPITTLGTIATLSSQVINPTAITVSAAQTTLTAAGGLTTPTITMQPVSQPTQV     960
TLITAPSGVEAQPVHDLPVSILASPTTEQPTATVTIADSGQGDVQPGTVTLVCSNPPCET    1020
HETGTTNTATTTVVANLGGHPQPTQVQFVCDRQEAAASLVTSTVGQQNGSVVRVCSNPPC    1080
ETHETGTTNTATTATSNMAGQHGCSNPPCETHETGTTNTATTAMSSVGANHQRDARRACA    1140
AGTPAVIRISVATGALEAAQGSKSQCQTRQTSATSTTMTVMATGAPCSAGPLLGPSMARE    1200
PGGRSPAFVQLAPLSSKVRLSSPSIKDLPAGRHSHAVSTAAMTRSSVGAGEPRMAPVCES    1260
LQGGSPSTTVTVTALEALLCPSATVTQVCSNPPCETHETGTTNTATTSNAGSAQRVCSNP    1320
PCETHETGTTHTATTATSNGGTGQPEGGQQPPAGRPCETHQTTSTGTTMSVSVGALLPDA    1380
TSSHRTVESGLEVAAAPSVTPQAGTALLAPFPTQRVCSNPPCETHETGTTHTATTVTSNM    1440
SSNQDPPPAASDQGEVESTQGDSVNITSSSAITTTVSSTLTRAVTTVTQSTPVPGPSVPP    1500
PEELQVSPGPRQQLPPRQLLQSASTALMGESAEVLSASQTPELPAAVDLSSTGEPSSGQE    1560
SAGSAVVATVVVQPPPPTQSEVDQLSLPQELMAEAQAGTTTLMVTGLTPEELAVTAAAEA    1620
AAQAAATEEAQALAIQAVLQAAQQAVMGTGEPMDTSEAAATVTQAELGHLSAEGQEGQAT    1680
TIPIVLTQQELAALVQQQQLQEAQAQQQHHHLPTEALAPADSLNDPAIESNCLNELAGTV    1740
PSTVALLPSTATESLAPSNTFVAPQPVVVASPAKLQAAATLTEVANGIESLGVKPDLPPP    1800
PSKAPMKKENQWFDVGVIKGTNVMVTHYFLPPDDAVPSDDDLGTVPDYNQLKKQELQPGT    1860
AYKFRVAGINACGRGPFSEISAFKTCLPGFPGAPCAIKISKSPDGAHLTWEPPSVTSGKI    1920
IEYSVYLAIQSSQAGGELKSSTPAQLAFMRVYCGPSPSCLVQSSSLSNAHIDYTTKPAII    1980
FRIAARNEKGYGPATQVRWLQETSKDSSGTKPANKRPMSSPEMKSAPKKSKADGQ        2035
```

FIG. 3A

HCF amino acid Feature Table

| # | Key | From | To | Shown... | Description |
|---|---|---|---|---|---|
| 1 | ACT SITE | 21 | 31 | Underline... | pep R60 |
| 2 | ACT SITE | 168 | 186 | Underline... | pep R37 |
| 3 | ACT SITE | 333 | 340 | Underline... | pep R52 |
| 4 | ACT SITE | 426 | 449 | Underline... | pep 362 |
| 5 | ACT SITE | 511 | 526 | Underline... | pep 329 |
| 6 | ACT SITE | 578 | 594 | Underline... | pep 223 first sequence |
| 7 | ACT SITE | 594 | 611 | Underline... | pep R26 first sequence |
| 8 | ACT SITE | 611 | 623 | Underline... | pep 223 second sequence |
| 9 | ACT SITE | 723 | 731 | Underline... | pep 318 |
| 10 | ACT SITE | 802 | 813 | Underline... | pep 299 |
| 11 | ACT SITE | 813 | 820 | Underline... | pep 268 |
| 12 | ACT SITE | 836 | 847 | Underline... | pep R26 second sequence |
| 13 | ACT SITE | 1010 | 1031 | Boxed/Fat... | repeat 1 |
| 14 | ACT SITE | 1072 | 1093 | Boxed/Fat... | repeat 2 |
| 15 | ACT SITE | 1101 | 1126 | Boxed/Fat... | repeat 3 |
| 16 | ACT SITE | 1158 | 1183 | Boxed/Fat... | repeat 4 |
| 17 | ACT SITE | 1286 | 1311 | Boxed/Fat... | repeat 5 |
| 18 | ACT SITE | 1314 | 1339 | Boxed/Fat... | repeat 6 |
| 19 | ACT SITE | 1349 | 1374 | Boxed/Fat... | repeat 7 |
| 20 | ACT SITE | 1414 | 1439 | Boxed/Fat... | repeat 8 |
| 21 | ACT SITE | 1774 | 1781 | Underline... | pep 293 second sequence |
| 22 | ACT SITE | 1808 | 1819 | Underline... | pep 115 |
| 23 | ACT SITE | 1819 | 1840 | Underline... | pep 261 first sequence |
| 24 | ACT SITE | 1853 | 1863 | Underline... | pep 240 |
| 25 | ACT SITE | 1901 | 1919 | Underline... | pep R32 |
| 26 | ACT SITE | 1919 | 1930 | Underline... | pep 261 second sequence |

FIG. 3B

"THE TNT" REPEAT

```
1    TLVCSNPPCETHETGTTNTATTTVVA
2    VRVCSNPPCETHETGTTNTATTATSN
3    QHGCSNPPCETHETGTTNTATTAMSS
4    AAQGSKSQCQTRQTSATSTTMTVMAT
5    TQVCSNPPCETHETGTTNTATTSNAG
6    QRVCSNPPCETHETGTTHTATTATSN
7    QQPPAGRPCETHQTTSTGTTMSVSVG
8    QRVCSNPPCETHETGTTHTATTVTSN

CON  QRVCSNPPCETHETGTTNTATTATSN
```

FIG. 3C

Nucleotide Sequence of HCF cDNA Clone

```
AGGCGGCTCAAGATGGCGGCTCCCAGGGCCTCCCGCCCGAGCTTGTAAGCGGGAGCGCCC    60
GGACAAGTAGTCGGGGCGACGGGACTCAGCGGCCTCCAGCTTCTTGAGCCTAGGCGCTCG   120
ACAGTTTCGGGCGGCTCTTGCGGAGACGGGGTGAGCGAGAAGAAAGGGAAGAGCCAAAGG   180
GAAGGAGGGCAGTTAAGATGGCGGCCTCCATGGAGTCGTCTACCGCTGTGTGAGAAACCG   240
CTTCTCCGTGAGAGCTGCCTTAGACGAAAGGGGGTGTGTGAAAGGAATTGAGGGCTCCC    300
TTCCCGCTTGTTGACTTCTCCCCACCGCACCCTTTCCCGGAACTATGGCTTCGGCCGTGT   360
CGCCCGCCAACTTGCCAGCGGTGCTTCTGCAGCCCCGCTGGAAGCGAGTGGTGGGCTGGT   420
CGGGTCCGGTGCCACGGCCCCGCCACGGCCACCGCGCCGTGGCCATCAAGGAGCTCATCG   480
TGGTGTTTGGCGGCGGCAACGAGGGAATAGTGGACGAACTGCACGTGTACAACACGGCAA   540
CCAACCAGTGGTTCATCCCAGCCGTGAGGGGGACATTCCCCCTGGGTGTGCAGCCTATG    600
GCTTCGTGTGTGACGGGACTCGCCTCCTGGTGTTTGGTGGGATGGTGGAGTATGGGAAAT   660
ACAGCAATGACCTCTACGAACTCCAGGCGAGCCGGTGGGAGTGGAAGAGACTCAAAGCAA   720
AGACGCCCAAAAACGGGCCCCCTCCGTGTCCTCGACTCGGGCACAGCTTCTCCCTTGTGG   780
GCAACAAATGCTACCTGTTTGGGGGTCTGGCCAATGATAGCGAGGACCCAAAGAACAACA   840
TTCCAAGGTACCTGAATGACTTATATATCCTGGAATTACGGCCAGGCTCTGGAGTGGTAG   900
CCTGGGACATTCCCATCACTTACGGGGTCCTACCACCACCCCGGGAGTCACATACTGCCG   960
TGGTCTACACCGAAAAAGACAATAAGAAGTCCAAGCTGGTGATCTACGGCGGGATGAGTG  1020
GCTGCAGGCTGGGGGACCTGTGGACCCTAGATATTGACACCCTGACGTGGAATAAGCCCA  1080
GTCTCAGCGGGGTGGCGCCTCTTCCTCGCAGTCTCCACTCGGCAACCACCATCGGAAATA  1140
AAATGTACGTGTTTGGTGGCTGGGTGCCTCTCGTCATGGATGACGTCAAAGTGGCCACAC  1200
ACGAGAAGGAGTGGAAGTGTACCAACACGCTGGCTTGTCTCAACCTGGATACCATGGCCT  1260
GGGAGACCATCCTGATGGATACACTGGAGGACAACATCCCCCGTGCTCGGGCTGGCCACT  1320
GCGCAGTCGCCATCAACACCCGCCTGTACATTTGGAGTGGGCGTGACGGCTACCGCAAGG  1380
CCTGGAACAACCAGGTCTGCTGCAAGGACCTCTGGTACCTAGAGACAGAAAAGCCACCAC  1440
CCCCAGCCCGAGTACAACTGGTACGCGCCAACACCAACTCCCTGGAGGTGAGCTGGGGGG  1500
CAGTGGCAACAGCCGACAGCTACCTTCTCCAGCTCCAGAAATATGACATTCCTGCCACGG  1560
CTGCTACTGCCACCTCCCCTACACCCAATCCGGTCCCATCTGTGCCTGCCAACCCTCCCA  1620
AGAGCCCTGCCCCAGCAGCAGCCGCACCTGCTGTGCAGCCGCTGACCCAAGTAGGCATCA  1680
CGCTCCTGCCCCAGGCTGCCCCCGCACCCCCGACCACCACCACCATCCAGGTCTTGCCAA  1740
CGGTGCCTGGCAGCTCCATTTCTGTGCCCACCGCAGCCAGGACTCAAGGTGTCCCTGCTG  1800
TTCTCAAAGTGACCGGTCCTCAGGCTACAACAGGAACTCCATTGGTCACCATGCGACCTG  1860
CCAGCCAGGCTGGGAAAGCCCCTGTCACCGTGACCTCCCTTCCCGCCGGAGTGCGGATGG  1920
TTGTGCCAACACAGAGTGCCCAGGGAACGGTGATTGGCAGTAGCCCACAGATGAGTGGGA  1980
TGGCCGCACTGGCCGCTGCGGCCGCTGCCACCCAGAAGATCCCCCCTTCCTCGGCACCCA  2040
CGGTGCTGAGTGTCCCAGCGGGTACCACCATCGTGAAGACCATGGCTGTGACACCTGGCA  2100
CTACCACCCTCCCAGCCACTGTGAAGGTGGCCTCCTCGCCAGTCATGGTGAGCAACCCTG  2160
CCACTCGCATGCTGAAGACTGCAGCCGCCCAGGTGGGGACATCGGTTTCCTCCGCCACCA  2220
ACACGTCTACCCGCCCTATCATCACAGTGCACAAGTCAGGCACTGTGACAGTGGCCCAGC  2280
AAGCCCAGGTGGTGACCACAGTTGTGGGCGGGGTCACCAAGACCATCACCCTGGTGAAGA  2340
GCCCCATCTCTGTCCCAGGAGGCAGTGCTCTGATTTCCAATCTGGGCAAAGTGATGTCGG  2400
```

FIG. 3D1

```
TGGTCCAGACCAAACCAGTTCAGACTTCAGCAGTCACAGGCCAGGCGTCCACGGGTCCTG    2460
TGACTCAGATCATCCAGACCAAAGGGCCCCTGCCAGCGGGAACAATCCTGAAGCTGGTGA    2520
CCTCAGCAGATGGCAAGCCCACCACCATCATCACTACCACGCAGGCCAGTGGGGCGGGGA    2580
CCAAGCCCACCATCCTGGGCATCAGCAGCGTCTCCCCCAGTACCACCAAGCCCGGCACGA    2640
CCACCATCATCAAAACCATCCCCATGTCGGCCATCATCACCCAGGCGGGCGCCACGGGTG    2700
TGACCAGCAGTCCTGGCATCAAGTCCCCCATCACCATCATCACCACCAAGGTGATGACTT    2760
CAGGAACTGGAGCACCTGCGAAAATCATCACTGCTGTCCCCAAAATTGCCACTGGCCACG    2820
GGCAGCAGGGAGTGACCCAGGTGGTGCTTAAGGGGGCCCCGGGACAGCCAGGCACCATCC    2880
TCCGCACTGTGCCCATGGGGGGTGTTCGCCTGGTCACACCCGTCACCGTCTCCGCCGTCA    2940
AGCCAGCCGTCACCACGTTGGTTGTGAAAGGCACCACAGGTGTCACGACCCTAGGCACAG    3000
TGACAGGCACCGTCTCCACCAGCCTTGCCGGGGCGGGGGGCCACAGCACTAGTGCTTCCC    3060
TGGCCACGCCCATCACCACCTTGGGCACCATTGCCACCCTCTCAAGCCAGGTGATCAACC    3120
CCACTGCCATCACTGTGTCGGCCGCACAGACCACGCTGACAGCGGCAGGCGGGCTCACAA    3180
CCCCAACCATCACCATGCAGCCCGTGTCCCAGCCCACCCAGGTAACTCTGATCACGGCAC    3240
CTAGTGGGGTGGAGGCCCAGCCTGTGCATGACCTCCCTGTGTCCATTCTGGCCTCCCCGA    3300
CTACAGAACAGCCCACCGCCACAGTTACCATCGCCGACTCAGGCCAGGGTGATGTGCAGC    3360
CTGGCACTGTCACCTTGGTGTGCTCCAACCCACCCTGTGAGACCCACGAGACTGGCACCA    3420
CCAACACGGCCACCACTACTGTTGTGGCTAACCTTGGGGGACACCCCCAGCCCACCCAAG    3480
TGCAGTTCGTCTGTGACAGACAGGAGGCAGCTGCTTCTCTTGTGACCTCGACTGTGGGCC    3540
AGCAGAATGGTAGCGTGGTCCGAGTCTGTTCGAACCCGCCCTGCGAGACCCACGAGACGG    3600
GCACCACCAACACCGCCACCACCGCCACCTCCAACATGGCCGGGCAGCATGGCTGCTCAA    3660
ACCCACCCTGCGAGACCCACGAGACGGGCACCACCAACACTGCCACTACAGCCATGTCGA    3720
GCGTCGGCGCCAACCACCAGCGAGATGCCCGTCGGGCCTGTGCAGCTGGCACCCCTGCCG    3780
TGATCCGGATCAGTGTGGCCACTGGGGCGCTGGAGGCAGCCCAGGGCTCTAAGTCCCAGT    3840
GCCAAACCCGCCAGACCAGCGCGACCAGCACCACCATGACTGTGATGGCCACCGGGGCCC    3900
CGTGCTCGGCCGGCCCACTCCTTGGGCCGAGCATGGCACGGGAGCCCGGGGGCCGCAGCC    3960
CTGCTTTTGTGCAGTTGGCCCCTCTGAGCAGCAAAGTCAGGCTGAGCAGCCCAAGCATTA    4020
AGGACCTTCCTGCGGGGCGCCACAGCCATGCGGTCAGCACCGCTGCCATGACCCGTTCCA    4080
GCGTGGGTGCTGGGGAGCCCCGCATGGCACCTGTGTGCGAGAGCCTCCAGGGTGGCTCGC    4140
CCAGCACCACAGTGACTGTGACAGCCCTGGAGGCACTGCTGTGCCCCTCGGCCACCGTGA    4200
CCCAAGTCTGCTCCAACCCACCATGTGAGACCCACGAGACAGGCACCACCAACACCGCCA    4260
CTACCTCGAATGCAGGCAGCGCCCAGAGGGTGTGCTCCAACCCGCCATGCGAGACCCACG    4320
AGACGGGCACCACCCACACGGCCACCACCGCTACTTCAAACGGGGGCACGGGCCAGCCCG    4380
AGGGTGGGCAGCAGCCCCCTGCTGGTCGCCCCTGTGAGACACACCAGACCACTTCCACTG    4440
GCACCACCATGTCGGTCAGCGTGGGTGCCCTGCTTCCCGACGCCACTTCTTCCCACAGGA    4500
CCGTGGAGTCTGGCCTAGAGGTGGCGGCGGCACCCAGCGTCACCCCCAGGCTGGCACCG    4560
CGCTGCTGGCTCCTTTCCCAACACAGAGGGTGTGCTCCAACCCCCCTGTGAGACCCACG    4620
AGACGGGCACCACTCACACGGCCACCACTGTCACTTCCAACATGAGTTCAAACCAAGACC    4680
CCCCACCTGCTGCCAGCGATCAGGGAGAGGTGGAGAGCACCCAGGGCGACAGCGTGAACA    4740
TCACCAGCTCCAGTGCCATCACGACAACCGTGTCCTCCACACTGACGCGGGCTGTGACCA    4800
CCGTGACGCAGTCCACACCGGTCCCGGGCCCCTCTGTGCCGCCCCCAGAGGAACTCCAGG    4860
```

FIG. 3D2

```
TGTCGCCAGGTCCTCGCCAGCAGCTGCCGCCACGGCAGCTTCTGCAGTCGGCTTCCACAG    4920
CCCTGATGGGGGAGTCCGCCGAGGTCCTGTCAGCCTCCCAGACCCCTGAGCTCCCGGCCG    4980
CCGTGGATCTGAGCAGCACAGGGGAGCCATCTTCGGGCCAGGAGTCTGCCGGCTCTGCGG    5040
TGGTGGCCACTGTGGTGGTCCAGCCACCCCCACCCACACAGTCCGAAGTAGACCAGTTAT    5100
CACTTCCCCAAGAGCTAATGGCCGAGGCCCAAGCTGGCACCACCACCCTCATGGTAACGG    5160
GGCTCACCCCCGAGGAGCTGGCAGTGACGGCTGCTGCAGAAGCAGCTGCCCAGGCCGCAG    5220
CCACGGAGGAAGCCCAGGCCCTGGCCATCCAGGCGGTGCTCCAGGCCGCGCAGCAGGCCG    5280
TCATGGGCACCGGCGAGCCCATGGACACCTCCGAGGCAGCAGCAACCGTGACTCAGGCGG    5340
AGCTGGGGCACCTGTCGGCCGAGGGTCAGGAGGGCCAGGCCACCACCATACCCATTGTGC    5400
TGACACAGCAGGAGCTGGCTGCCCTGGTGCAGCAGCAGCAGCTGCAGGAGGCCCAGGCCC    5460
AGCAGCAGCATCACCACCTCCCCACTGAGGCCCTGGCCCTGCCGACAGTCTCAACGACC    5520
CAGCCATTGAGAGCAATTGCCTCAATGAGCTGGCCGGCACGGTCCCCAGCACTGTGGCGC    5580
TGCTGCCCTCAACGGCCACTGAGAGCCTGGCTCCATCCAACACATTTGTGGCCCCCCAGC    5640
CGGTTGTGGTGGCCAGCCCAGCCAAGCTGCAGGCTGCAGCTACCCTGACCGAAGTGGCCA    5700
ATGGCATCGAGTCCCTGGGTGTGAAGCCAGACCTGCCGCCCCCACCCAGCAAAGCCCCCA    5760
TGAAGAAGGAAAACCAGTGGTTTGATGTGGGAGTCATTAAGGGCACCAATGTAATGGTGA    5820
CACACTATTTCCTGCCACCAGATGATGCTGTCCCATCAGACGATGATTTGGGCACCGTCC    5880
CTGACTATAACCAGCTGAAGAAGCAGGAGCTGCAGCCAGGCACAGCCTATAAGTTTCGTG    5940
TTGCCGGAATCAATGCCTGTGGCCGGGGGCCCTTCAGCGAAATCTCAGCCTTTAAGACGT    6000
GCCTGCCTGGTTTCCCAGGGGCCCCTTGTGCCATTAAAATCAGCAAAAGTCCGGATGGTG    6060
CTCACCTCACCTGGGAGCCACCCTCTGTGACCTCCGGCAAGATTATCGAGTACTCCGTGT    6120
ACCTGGCCATCCAGAGCTCACAGGCTGGGGCGAGCTCAAGAGCTCCACCCCGGCCCAGC    6180
TGGCCTTCATGCGGGTGTACTGTGGGCCCAGCCCTCCTGCCTGGTGCAGTCCTCCAGCC    6240
TTTCCAACGCCCACATCGACTACACCACCAAGCCCGCCATCATCTTCCGCATCGCCGCCC    6300
GCAATGAGAAGGGCTATGGCCCGGCCACACAAGTGAGGTGGCTGCAGGAAACCAGTAAAG    6360
ACAGCTCTGGCACCAAGCCAGCCAACAAGCGGCCCATGTCCTCTCCAGAAATGAAATCTG    6420
CTCCAAAGAAATCTAAGGCCGATGGTCAGTGAGAGGAAGCTGACTAGCCCCTGGATTCTT    6480
CTCCAGACCCCCTGCTTCAGGAACACCCGCCAGGGCCCACCCCTCCCACCCCGTCCCAG    6540
CATTCGCACTTCACCCTCGCGAGCCGCTGTTCACTCCTCTCCCCTTTCTCTTTCTCTCTG    6600
TTTTTAAAATAATCTAAAGAAAGCACATTTTACCATTGCTGTTGGGAGGAAGCAGAGGCA    6660
GATGGGAAAGCAGAGAGAGGAGCGCGCTTCCTTTCCTCCCCGCTGCCGCCCACCCTGGGG    6720
AGAGACTTTTGCGGGGAGGGAAGGCGGAGCTGAGGACAGCCAGCTCCGCCCTCCCAAGGC    6780
TGTGCGTTCCTGAGGGCCAGGTCGGGGCAGGCATGGAGGGGAGGAAAGGCGTCCCTCTT    6840
GGCCCTCCCCAGAGTGGCTTTCCTGGCACCCTGGCCTGGGTGTCTGGTTCTGTTTTCTTT    6900
TCTTCCCCTTGTGTTTCCAGTCACCTAACTTCCCTTCCTCAGGCTCCCCGGCCCACCCT    6960
GCTCAGTGACCCCACAGGAAGCTTACACATTTTCTCAGAGGCCTTTGTGCTCCCACCTCT    7020
TCTACCCTCCCCCTCTTCTTTCCCATTTTAAAAAGAAAAGAAGGAAAAAGAAAAAAGGG    7080
GCAAGGAGCCCCGCGGCGGCCTGGGCAGCGCCTGTGCAGACCTCCCTGCAGGCCGCACTG    7140
CCAACTGCTGCATTTGTTGTGTTTTTAGGTTGCAATTGGTGAAGTTCACACTTTCATTG    7200
TAATTTTAGCGTGTGGGGTTTTGTCCCTTTTTTGTTGTTGTTAGCTGTGTACAGAATGTG    7260
TAACCTTTTTTCTTTTCTCTTTTTTTTGTTTTGTTTTGTTTTGTTTTTTACTTT        7320
```

FIG. 3D3

```
TTTCTTCTTGGCTAATTCTTGGCAGGGATCTTTCTGGAGGAAAAGCTGGGGCCAGCCAGG 7380
GCAGGAGAGGTGTGAAATCTGCCACGAGGGGCCTGCTGTTTGCCACCCAGCCCAACTTCC 7440
TGTTGCTGGCCCCTGCCCTCTGCCCTTTTGCCTGTCCTCAGGCCGCTGGAACAAAGGAAG 7500
GACAGCTCATTCCTCATGGGCGATCACTCCGCATCTATAGGGTCGAGCCTAGGGGAGCTT 7560
GAGGGAGGGCTGGGGCCTCCTTGTCCTGGATTTCCAGCTCTCCCCATCCCCCCTCCCTGA 7620
GCACCACCGGCACCGCCTCCCAAACAGGGCTGCTGGTTTCCGCAGCCACTGCTCCACCTC 7680
CCCCAAATCGTCATGGAAAGGGTGGAGATGGAGGGGAACCAGGCGTCCTTGGAGGCAGCT 7740
TGGGAGGGTGACTGTGTAGTGTCACCCACAAGGGAGGCTAGGGCAATGGAGCAGGCCACC 7800
AGCAGCAGCTGTGCAGCATGGAACTCAGGCCAGGCTCCGAGGCTGGGGATCTGCTTGGA 7860
GTTTTCTGCCCCCCACCCCAAACTTCTGTCGAGGAGCAAGGCTTGCCAGCAAGTCAGAAG 7920
GATTTGAACCGAGCAGCCAATCTTTCCAGCCCTCCCCTACCGACCTCTGCCTGGAGACGC 7980
AGCAGCCTGTGTCCTCCAGGGCCTCTGGTTTGTTGTATTATAGTATATTTCGCTGTGGAA 8040
AATGTCACGTTTAGTCACCTTGGAGCCCACTCACCTGGTCCTGTTGTTTTACCCCATCCC 8100
TTCTCTCGCGCGCCTATTGATTTGTTTCTGAGGAGAGTACACCGTTCACTATTGTAGAGT 8160
AACCCCTGTGACTCAATATTACCATAGTGCGATGTCGTTTTGTGCTATTTTGAACAATTA 8220
AAAGACTTTTTTTGAAATAAAAAAAAAAAAAAA                            8252
```

EUKARYOTIC TRANSCRIPTION PROTEIN; HOST CELL FACTOR

The research carried out in the subject application was supported in part by grants from the National Institutes of Health. The government may have rights in any patent issuing on this application.

CROSS-REFERENCE TO RELATED APPLICATIONS

This application is a continuation-in-part of application Ser. No. 07/989,842, filed Dec. 4, 1992, abandoned, the disclosure of which is hereby incorporated by reference.

INTRODUCTION

1. Technical Field

The technical field of this invention concerns Host Cell Factor, HCF, a eukaryotic cellular protein involved in transcription, nucleic acids encoding HCF, and methods of using HCF and HCF encoding nucleic acids.

2. Background

Approximately half the United States population is infected with Herpes Simplex Virus type 1 (HSV-1). The usual mode of HSV-1 infection is by direct person-to-person contact in early life—usually at abrasions around the mouth and lips. The initial infection is most often asymptomatic resulting in latent viral infection of the trigeminal ganglia. HSV-1 presents clinically as recurrent orolabial lesions heralded by a prodrome of pain, burning, or itching. Lesions typically last about ten days and reoccur with a period between one and twelve months.

Herpes Simplex Virus type 2, or genital herpes, is an extremely wide spread and serious sexually transmitted disease. About a quarter of the U.S. population is infected with HSV type 2. Infection occurs primarily in adolescents and young adults, resulting in illness lasting several weeks. Multiple lesions occur on the genitalia, which in females are often excruciatingly painful.

HSV (types 1 and 2) patients compromised by either immune therapy, underlying disease, or immune suppression may suffer from more severe, disseminated lesions. There is no cure for HSV infection. Acyclovir, the only current treatment, may cause fetal abnormalities and maternal toxicity, can lead to the emergence of less sensitive or resistant virus, and does not eliminate latent HSV.

Efficacious treatment of viral diseases is the holy grail of the pharmaceutical industry. Much of this industry's current efforts are focused on identifying viral-specific drugs. Ideal treatments for viral infections are those that specifically interfere with viral function, such as viral-specific transcription. The HSV transcription factor VP16 presents an ideal target for drug targeting. Unfortunately, the complexity of VP16-mediated HSV transcription has made it impossible to assemble the components required for efficient assays for identifying potential VP16-targeted drugs.

VP16 transactivates HSV immediate early (IE) genes. The IE promoter regions contain 5'-TAATGARAT-3' (SEQ ID NO: 01) elements that are frequently overlapped by octamer element related sequences to yield a sequence such as 5'-ATGCTAATGARAT-3' (octamer element underlined). IE gene activation appears to require the interaction of this promoter region with a complex of VP16, Oct1 or a related protein, and a nuclear fraction, variously termed host cell factor (HCF), Cl, VCAF, and CFF. Until the present disclosure, HCF has defied characterization and identification. Without a source of recombinant HCF, it is not possible to assemble a defined assay for VP16-mediated transcription. Accordingly, the present invention provides the pharmaceutical industry with the critical, missing ingredient for Herpes virus drug development.

Relevant Literature

Kristie and Sharp (1993), J Biol Chem 268, 6525–6534; Stem and Herr (1991), Genes and Development 5, 2555–2566; Xiao and Capone (1990), Molecular and Cellular Biology 10 (9), 4974–4977; Kristie and Sharp (1990), Genes and Development 4, 2382–2396; Haigh, et al. (1990), Nature 344, 257–259; Katan et at. (1990), Nucleic Acids Research 18, 6871–6880; Kristie et al. (1989) EMBO J. 8, 4229–4238; Gerster and Roeder (1988) Proc Natl Acad Sci USA 85, 6347–6351; and Stem et al. (1989), Nature 341, 624–630 relate to the VP 16 transcription complex.

SUMMARY OF THE INVENTION

Host Cell Factor (HCF), related eukaryotic nuclear proteins involved in transcription, nucleic acids encoding HCF, and methods of using HCF and HCF-encoding nucleic acids are provided. HCF activity comprises a collection of polypeptides encoded by a single structural gene encoding a parent protein of about 2039 amino acids. HCF-specific binding compounds are disclosed including antibodies to HCF epitopes. HCF is required for the transcription of a number of viral genes, such as the immediate early Herpes simplex virus I genes. The invention provides HCF-based pharmaceutical compositions and HCF-based methods for screening chemical libraries for regulators of viral transcription. Such compositions are used in the treatment of viral infections by modulating the transcription of certain viral genes, especially those whose promoters contain the TAATGARAT element.

(A) Diagram depicting the purification scheme. For details see Experimental Procedures.

(B) HCF-associated polypeptides fall into three size classes. A representative HCF preparation was electrophoresed on a 7% SDS-polyacrylamide gel and visualized by silver staining. The relative mobilities and sizes (in KDa) of the molecular weight markers (lane M) are indicated.

(C) Glycerol gradient sedimentation of HCF. Aliquots (10 microliters) from each fraction were analyzed on a 6% SDS-polyacrylamide gel. Proteins were stained with silver. The sizes of the protein molecular weight markers are given on the left. An aliquot of the load material (10 ul) is also shown on the left.

(D) Sedimentation of HCF activity. The fractions shown in panel C were tested for HCF activity by gel mobility-shift assay. An aliquot of each fraction was diluted ten-fold in fetal calf serum (included to prevent non-specific protein loss) and 1 ul of this was assayed with GST-VP16, Oct-1 POU domain, and labeled (octa+)TAATGARAT probe. Unbound probe is shown on the left (lane a) followed by probe mixed with HeLa nuclear extract (lane b), and probe mixed with HeLa extract, Oct-1 POU domain, and GST-VP16 (lane c). The positions of the Oct-1 POU domain complex, Hela cell Oct-1 complex (Oct-1), and VP16-induced complex (VIC) are shown on the left. The asterisks indicates a weak HCF-independent VIC complex that is stabilized by the fetal calf serum in the reaction mixture.

FIG. 3. Structure of HCF. (A) The deduced amino acid sequence of the cDNA encoding HCF (SEQ ID NO: 05). Peptides corresponding to those obtained from the purified protein species are boxed. The peptide number and parent protein band from which the amino acid sequence was obtained are given below the box; parent protein nomenclature is given in FIG. 2. The deduced amino acid sequence of the H12 insert is indicated by a bar. The two guessmers used to isolate H12 are indicated above their parent peptides. The sequences were as follows: gs-1, 5'GAG AAC CAG TGG TIT GAT GTG GGC GTG ATC AAG 3' (SEQ ID NO: 02); gs-2, 5' AAG CAG GAG CTX CAG CCT GGC ACA GCC TAC AAG 3' (SEQ ID NO: 03). (B) Table indicating peptide (underlined) and repeat (boxed) sequences of FIG. 3A. (C) Consensus sequence of "THE TNT" repeat (SEQ ID NO: 014). (D1)–(D4) Diagram of the HCF cDNA (SEQ ID NO: 015). The underlined positions include the start codon (nucleotide positions 345–347), the stop codon (6450–6452), and the poly A signal sequence (8216–8223).

Figure 4:
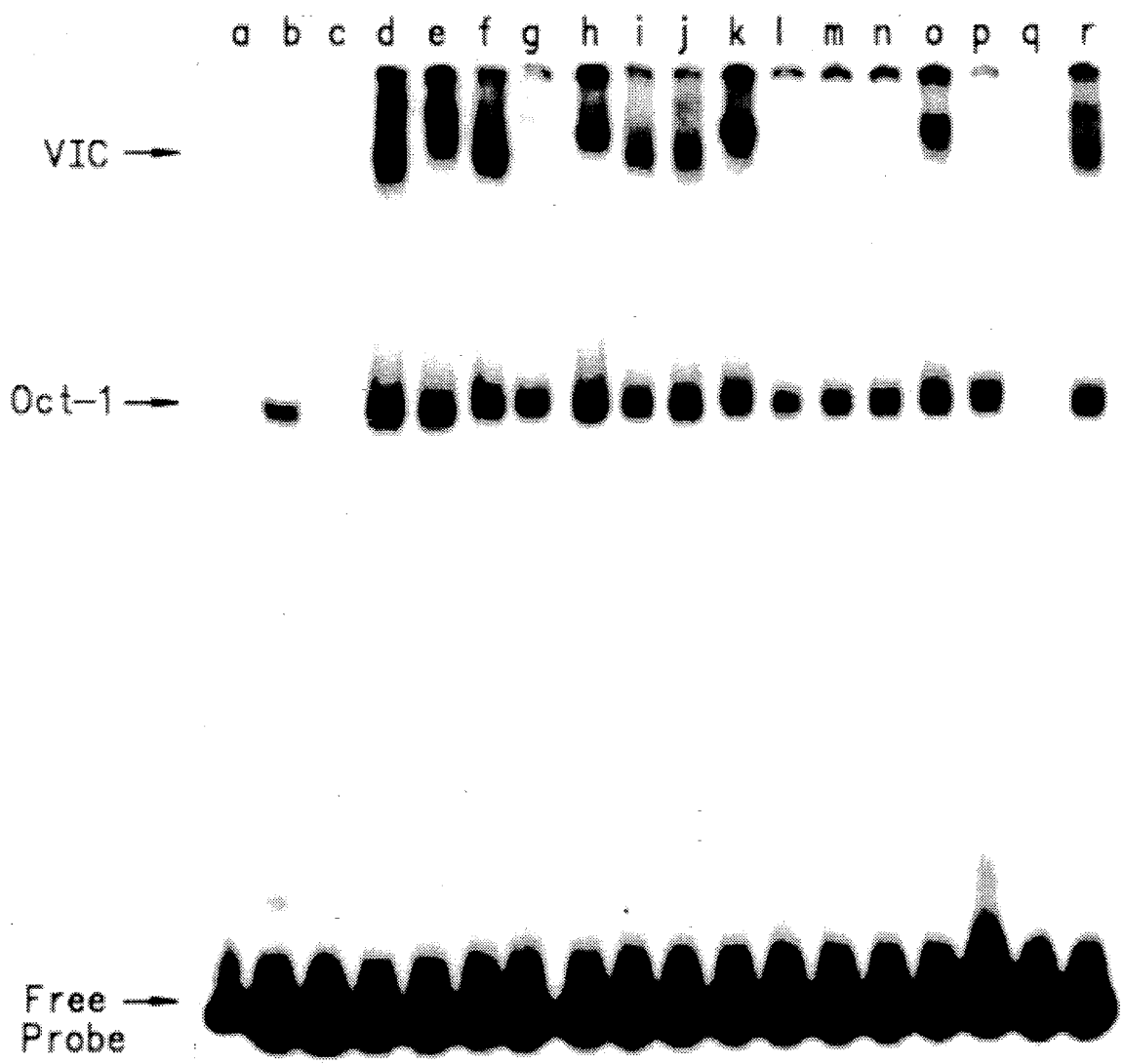

FIG. 4. Disruption of VIC by antibodies to HCF. A WGA fraction containing HCF activity was preincubated in the presence of various amounts of antisera prior to addition of the remaining EMSA reagents. a, probe alone; b, WGA fraction, no GST-VP16DC added; c, GST-VP16DC, no WGA fraction added; d-o, and r, WGA fraction plus GST-VP16DC: e, 1:100 dilution of LP1 antibody to VP16; f, 1:10 dilution of preimmune mouse serum; g, 1:10 dilution of mouse antiserum to purified HCF; h, 1:50 dilution of mouse antiserum to purified HCF; i, 1:100 dilution of mouse antiserum to purified HCF; j, no addition; k, 1:10 dilution of preimmune rabbit serum; 1, 1:10 dilution of antiserum to rHCF; m, 1:100 dilution of rabbit antiserum to rHCF; n, 1:500 dilution of rabbit antiserum to rHCF; 0, 1:5000 dilution of rabbit antiserum to rHCF; p, WGA extract plus 1:10 dilution of rabbit antiserum to rHCF; q, GST-VP16DC plus 1:10 dilution of rabbit antiserum to rHCF; r, 1:100 dilution of control antibody 12CA5. VIC, VP16-induced complex; Oct-1, Oct-1—DNA complex; Free probe, $^{32}$P-labeled DNA containing the TAATGARAT element from the ICPO gene.

Figure 5C:
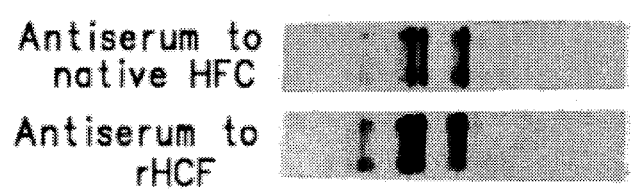
Figure 5B:
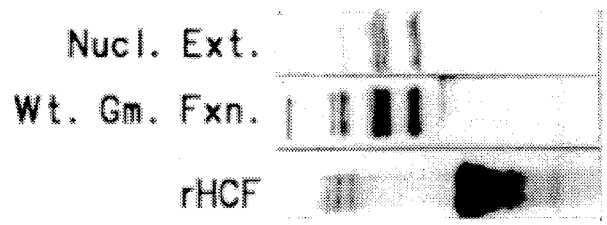
Figure 5A:
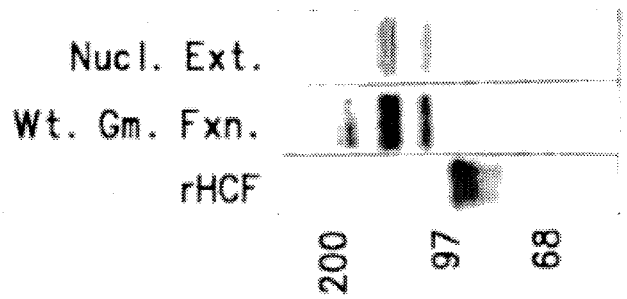

FIG. 5. Multiple forms of HCF are recognized by antiserum to recombinant HCF. Extracts were subjected to SDS PAGE, and proteins were transferred to nitrocellulose, incubated with antisera to either a purified HCF fraction (native HCF) or recombinant HCF, and visualized by the alkaline phosphatase method (Sambrook et. al. supra). rHCF, recombinant HCF; Wt. Gm Fxn., wheat germ agglutinin fraction; Nucl. ext., nuclear extract.

Figure 6:
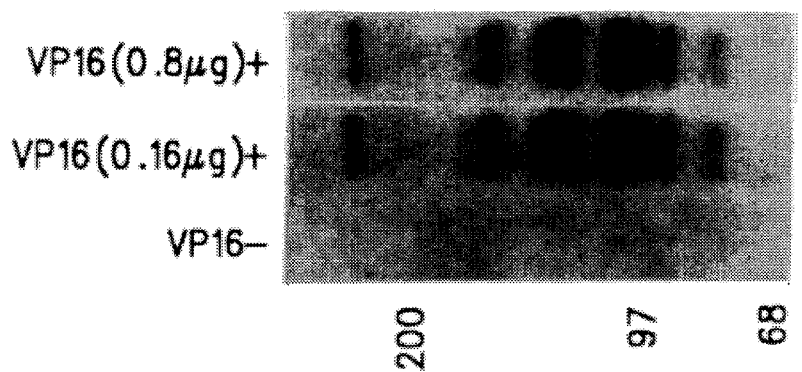

FIG. 6. HCF can be immunoprecipitated from VP16-supplemented HeLa cell extracts with an antibody to VP16. GST-VP16DC was added to freshly prepared HeLa extracts and HCF polypeptides were co-immune precipitated with the LP1 antibody. Immune complexes were subjected to SDS PAGE on a 7% acrylamide gel, transferred to nitrocellulose, and visualized with rabbit antiserum to rHCF and $^{125}$I-protein A. Additions to the extracts are indicated above each lane.

DESCRIPTION OF SPECIFIC EMBODIMENTS

Host Cell Factor (HCF), nucleic acids encoding HCF, and methods of use are provided.

As used herein, HCF refers to translation products of a nucleotide sequence substantially homologous with the disclosed HCF nucleotide sequence. HCF may be recombinant or purified from a natural source and includes xenogeneic HCF analogs. HCF translation products frequently have native post-translational modifications such as glycosylation patterns.

A polypeptide comprising an "epitope" of HCF comprises a three-dimensional structural conformation presented by a translation product of the disclosed HCF gene. Such an epitope is structurally distinguished from previously known epitopes. While an epitope is functionally defined in terms of a spatial conformation, typically epitopes are characterized by amino acid sequence homology to at least a "portion" of the disclosed HCF amino acid sequence or by antibodies, preferably monoclonal antibodies, which are capable of specifically binding a translation product of the disclosed HCF gene.

A "portion" of HCF is a peptide sequence unique to HCF in that it is not found in any previously known proteins. Thus a portion has an amino acid sequence length at least long enough to define a novel polypeptide. A portion of HCF is a polypeptide of at least about a six, preferably at least about an eighteen, more preferably at least about a thirty-six amino acid sequence of HCF and may be as long as the full length HCF of about 2039 amino acids. Portions of HCF are readily identified from the disclosed HCF amino acid sequence (SEQ ID NO: 05) by comparison to known protein sequence data bases.

"Xenogeneic" HCF analogs are nonhuman-derived proteins with substantial functional or sequence identity to HCF. Nonhuman sources of xenogeneic HCF analogs include animal sources, such as Drosophila, Spodoptera, and preferably mammalian. Of particular interest are rodents, primates, and livestock animals including bovine, ovine, equine and avian species "Functional" HCF analogs or proteins with "substantial functional identity" to HCF are compounds that exhibit one or more biochemical properties specific to HCF, such as the ability to specifically modulate the transcription of one or more TAATGARAT or octamer element containing genes; or, the capacity to facilitate VP16 association with Oct1 and TAATGARAT. Preferably, such proteins are also capable of specifically binding VP16 under conditions such as described herein.

"Substantial sequence identity" or "substantially homologous" means that a portion of the polypeptide presents at least about 70%, more preferably at least about 80%, and most preferably at least about 90% sequence identity with an HCF sequence portion. Where the sequence diverges from HCF, the differences are preferably conservative, i.e. an acidic for an acidic amino acid substitution or a nucleotide change providing a redundant codon. Dissimilar sequences are typically aggregated within regions rather than being distributed evenly over the polymer.

"Modulating transcription" means altering transcription, and includes changing the rate or level of transcription and changing the responsiveness of transcription to regulatory controls.

An "isolated" polypeptide or nucleic acid is unaccompanied by at least some of the material with which it is associated in its natural state. Generally, an isolated polypeptide constitutes at least about 1%, preferably at least about 10%, and more preferably at least about 50% by weight of the total protein in a given sample. Included in the polypeptide weight are alternative forms such as differentially glycosylated or phosphorylated or otherwise post-translationally modified forms. Stained bands of a polypeptide are readily identified by Coomassie staining when the polypeptide, in isolated form, is subjected to electrophoresis according to the method of Laemmli, U.K. (1970) Nature 227, 680–685. A composition comprising substantially pure polypeptide is at least about 10%, preferably at least about 30%, more preferably at least about 70% by weight total protein. By pure polypeptide is intended at least about 90%, preferably at least 95%, and more preferably at least about 99% by weight of protein. Protein weight percentages are determined by dividing the weight of HCF, including alternative forms of HCF and HCF analogs such as alternatively spliced, differentially phosphorylated or glycosylated, or otherwise post-translationally modified HCF, present in a fraction by the total protein weight present. Experimental methods for purifying HCF are set out below and in the following working exemplification.

An "isolated" nucleic acid sequence is present as other than a naturally occurring chromosome or transcript in its natural state and typically is removed from at least some of the nucleotide sequences with which it is normally associated with on a natural chromosome. A sequence substantially identical or homologous to an HCF epitope-encoding sequence hybridizes to a complementary HCF epitope-encoding sequence under low stringency conditions, for example, at 50° C. and SSC (0.9M saline/0.09M sodium citrate) and that remains bound when subject to washing at 55° C. with SSC. A partially pure nucleotide sequence constitutes at least about 5%, preferably at least about 30, and more preferably at least about 90% by weight of total nucleic acid present in a given fraction. The nucleic acids of the invention and portions thereof, other than those used as PCR primers, are usually at least about 60 bp and usually less than about 6 kb in length. PCR primers are generally between about 15 and 100 nucleotides in length.

Of particular interest are portions of HCF that facilitate HCF functional or structural interaction with transcription associated factors, particularly TAATGARAT or octamer element associated transcription factors, more particularly, Oct1. Of special interest are portions of HCF that interact with VP16, and with a combination of Oct1, VP16 and DNA, and subcombinations thereof. For example, HCF can specifically bind VP16 even in the absence of DNA and Oct1. The identification of such portions is disclosed below.

Specific binding is empirically determined by contacting, for example HCF, with a mixture of components and identifying those components that preferentially bind HCF. For instance, in the case of DNA, DNA binding, specificity may be shown by competitive binding of specific (substantially complementary)- over nonspecific-oligonucleotides. Specific binding is most conveniently shown by gel shift assays with competitor DNA or by immobilizing, for example HCF, on a solid matrix such as a polymer bead or microtiter plate and contacting the immobilized HCF with a mixture. Often, one or more components of the mixture will be labelled. Another useful approach is to displace labelled ligand, like VP16, from an immobilized target, like HCF. Alternatively, the immobilized component can be VP16 and the soluble component HCF. Generally, specific binding of HCF will have binding affinity of 10–6M, preferably 10–8M, more preferably $10^{-10}$M, in the presence of Oct1, TAATGARAT and VP16 at 30° C.

Epitopes of HCF find use in defining functional domains of HCF, identifying compounds that associate with HCF, designing compounds capable of modifying transcription, for example, by binding or modulating an epitope of HCF or exploiting structural features of HCF to directly modify gene expression, and the like. In an analogous situation, a VP16-derived peptide has been reported to inhibit in vitro formation of the HSV transcription complex, Haigh et al. (1990) supra. Accordingly, peptides encoding HCF epitopes are provided that are capable of interfering with HSV transcription complex formation or modulating functional domains of HCF. Typically, such peptides are effective by competitively inhibiting an HCF domain's association with another compound, typically a protein or DNA. Preferred HCF-derived peptides are capable of interfering with the transcription of TAATGARAT or octamer element containing genes; more preferably, with HCF-VP16 association.

For example, the amino acid sequence approximately bounded by Glu22 and Glu245 comprises a highly negatively charged region. Peptides from this region find particular use as immunogens and as modulators of HCF-protein interactions. Additionally, the sequence approximately bounded by Lys286 and Lys345 comprises a highly positively charged region. Peptides from this region find particular use as immunogens and modulators of HCF-protein and HCF-nucleic acid interactions. Of particular interest are peptides approximately bounded by Glu73 and Glu121.

Associational domains of HCF are ascertainable by those skilled in the art using the methods and compositions disclosed herein. For example, HCF mutants, including deletion mutants can be generated from the disclosed HCF sequence and used to identify regions important for specific protein or nucleic acid interactions. Alternatively, the ability of HCF deletion mutants to support in vitro transcription or in vivo transcription in transfection assays is determined.

The invention provides recombinantly produced HCF, HCF analogs and portions thereof. These recombinant products are also readily modified through physical, chemical, and molecular techniques disclosed or cited herein or otherwise known to those skilled in the relevant art. A preferred baculovirus expression system permits the recombinant HCF to be modified, processed and transported within a eukaryotic system. According to a particular embodiment of the invention, portions of the HCF encoding sequence are spliced, using recombinant DNA technology, with heterologous sequences to produce fusion proteins. Such fusion proteins find particular use in modulating gene transcription.

For example, domains of HCF can be fused to a well-characterized DNA binding domain (see, e.g., Sadowski et at., (1988) Nature 335, 563–564) and the resulting fusion protein can be tested for its ability to activate transcription. In this way, HCF transcription activation domains are identified. Alternatively, an HCF domain can be fused with a domain having endonuclease activity for site-specific DNA cleaving. Other useful HCF fusion partners include GST, Lerner epitope, an epitope recognized by a monoclonal antibody (e.g. hemagglutinin epitope and 12CA5 monoclonal antibody), glutathione S-transferase for immobilization, the VP16 activation domain, etc.

The invention also provides for functional and structural analogs of HCF. Using biochemical and molecular methods either known in the art or disclosed herein, the disclosed HCF and nucleotide sequences are used to generate non-natural analogs of HCF. Such analogs find use as HCF antagonists, reagents for use in drug screening assays, particularly drugs effective for HSV infection, reagents for modulating transcription of TAATGARAT or octamer element containing genes, etc.

For example, the disclosed HCF sequence contains numerous serine residues which are useful sites for phosphorylation or dephosphorylation. See e.g. methods disclosed in Roberts et al. (1991) Science 253, 1022–1026 and in Wegner et al. (1992) Science 256, 370–373.

The disclosed sequences are also used to identify and isolate natural HCF analogs. Such analogs include natural human analogs as well as xenogeneic analogs (non-human HCF). For example, an HCF activity has been identified in non-human cells, specifically, Drosophila cells.

Further, many transcription factors belong to families, for example, the Oct family includes Oct1, Oct2 and Oct3/4 and C/EBP has C/EPBP,$_\alpha$, $_{\beta and\ \gamma}$—the members of which are expressed differentially, for example at different developmental periods or tissue specifically. Accordingly, the disclosed compositions and methods are used to identify, characterize, isolate, and purify such HCF-related proteins. For example, oligonucleotides encoding functional domains of HCF are $^{32}$P-labeled and used to screen λcDNA libraries at low stringency to identify similar cDNAs that encode proteins with related functional domains. Additionally, HCF related proteins are isolated by antibody cross reactivity and PCR amplification with degenerate oligonucleotide probes using the sequences disclosed herein.

HCF can be further modified by methods known in the art. For example, HCF is phosphorylated or dephosphorylated, glycosylated or deglycosylated, with or without radioactive labeling, etc. Phosphorylation may be involved in modulating the transcription activation activity of CREB proteins, C/EBP$_\alpha$, VP16, Oct1, Oct2, etc. Especially useful are modifications that alter HCF solubility, membrane transportability, stability, and binding specificity and affinity. Some examples include fatty acid-acylation, proteolysis, and mutations in VP16 interaction domains that stabilize binding.

HCF may also be modified with a label capable of providing a detectable signal, for example, at a heart muscle kinase labeling site, either directly or indirectly. Exemplary labels include radioisotopes, fluorescers, etc. Such labeled HCF and analogs thereof find use, for example, as probes in expression screening assays for proteins that interact with HCF, or, for example, HCF binding to VP16 in drug screening assays.

Specific polyclonal or monoclonal antibodies that can distinguish HCF from other nuclear proteins are conveniently made using the methods and compositions disclosed in Harlow and Lane, Antibodies, A Laboratory Manual, Cold Spring Harbor Laboratory, 1988, other references cited herein, as well as immunological and hybridoma technologies known to those in the art. Where HCF derived peptides are used to induce an HCF-specific immune response, the peptides may be conveniently coupled to an suitable carrier such as KLH and administered in a suitable adjuvant such as Freunds. In particular, selected peptides were coupled to a lysine core carder substantially according to the methods of Tam (1988) Proc Natl Acad Sci USA 85, 5409–5413.

Also provided are other compounds that specifically bind HCF and are obtained using immunologic, chromatographic or synthetic methods available to those skilled in the art. For example, using the procedure of PCT applications WO 84/03564, WO 84/03506, WO 86/00991, specifically binding oligopeptides may be prepared synthetically. Of particular interest are HCF-specific antibodies that can be modified to a monovalent form, such as Fab, Fab', or Fv. Anti-idiotypic antibody, especially internal imaging anti-ids are also prepared using the disclosures herein.

Anti-HCF antibodies find use, for example, in blocking HCF involvement in transcription complexes. In addition, these antibodies can be used to identify, isolate, and purify structural analogs of HCF. Anti-HCF antibodies also find use for subcellular localization of HCF under various conditions such as HSV infection, during various cell cycle phases, induction with cytokines, protein kinases such as C and A, etc. Other exemplary applications include using HCF-specific antibodies (including monoclonal or HCF-derived peptide antibodies) to immuno-deplete in vitro transcription extracts and using immuno-affinity chromatography to purify HCF, including analogs, or other nuclear factors which interact with HCF.

A wide variety of protocols are available for performing immunoassays, sequencing nucleic acid and peptide sequences, and any or all of these may be employed, depending upon the particular situation. Immunoassays include ELISA, EMIT, CEDIA, SLIFA, and the like. A number of diagnostic procedures have been described in variety of issued patents such as U.S. Pat. Nos. 3,791,932; 3,817,837; 3,998,943, and references cited therein.

The present invention discloses the purification of HCF by wheat germ agglutinin affinity chromatography. Accordingly, the invention provides glycosylated HCF, particularly, HCF containing at least an N-acetylglucosamine moiety, and for modifications to HCF glycosylation. For example, glycosidases and lectins are used to modify, including labelling, or purify HCF with particular glycosidation patterns. Such modifications can effect changes in HCF localization, stability, binding specificity, etc.

Compositions are also provided for therapeutic intervention in disease, for example, by modifying HCF or HCF encoding nucleic acids. Oligopeptides can be synthesized in pure form and can find many uses in diagnosis and therapy. These oligopeptides can be used, for example, to modulate native HCF interaction with native transcription factors or DNA. The oligopeptides will generally be more than six and fewer than about 60 amino acids, more usually fewer than about 30 amino acids, although large oligopeptides may be employed. If desired, the entire HCF molecule may be employed, but it will be frequently convenient to use a portion thereof. HCF or a portion thereof may be used in purified form, generally greater than about 90%, usually greater than about 95% pure. Methods for purifying such peptides to such purities include various forms of chromatographic, chemical, and electrophoretic separations disclosed herein or otherwise known to those skilled in the art.

HCF ENCODING NUCLEIC ACID

The invention provides nucleic acid sequences encoding an HCF epitope, including sequences substantially identical or homologous to sequences encoding an HCF epitope. Included are DNA and RNA sequences, sense and antisense. The nucleotide (cDNA) sequence encoding full length HCF (SEQ ID NO: 15) is disclosed in FIG. 3. The disclosure also provides for the disclosed HCF encoding sequence modified by transitions, transversions, deletions, insertions, or other modifications such as alternative splicing. The invention also provides for genomic HCF sequences, HCF gene flanking sequences, including HCF regulatory sequences.

For modified HCF-encoding sequences or related sequences encoding proteins with HCF-like functions, there will generally be substantial sequence identity between at least a portion thereof and a portion of HCF, preferably at least about 40%, more preferably at least 80%, most preferably at least 90%, particularly conservative substitutions, particularly within regulatory regions and regions encoding protein domains involved in protein-protein interactions, particularly HCF-VP16 interactions.

Typically, the invention's HCF encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein.

Sequences encoding xenogeneic HCF are also provided. For example, HCF specific or related sequences within a genome of a nonhuman species are localized using Southern hybridization techniques. Also, the HCF encoding nucleic acids can be subject to alternative purification, synthesis, modification or use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, New York, 1992) or that are otherwise known in the art.

For example, the nucleic acids can be modified to alter stability, solubility, binding affinity and specificity, etc. For example, HCF encoding sequences can be selectively methylated, etc. The nucleic acid sequences of the present invention may also be modified with a label capable of providing a detectable signal, either directly or indirectly. Exemplary labels include radioisotopes, fluorescers, biotinylation, etc.

Additionally, cDNA encoding at least a portion of HCF is useful for characterizing tissue specific expression of HCF as well as changes of HCF expression over time, particularly during organismal development or cellular differentiation. Further, using expression screening in yeast as described in Current Protocols in Molecular Biology (supra), nucleic acids encoding at least a portion of HCF are used to identify nuclear factors which interact with HCF. In this example, a yeast eDNA library containing fusion genes of eDNA joined with DNA encoding the activation domain of a transcription factor (e.g. Gal4) are transfected with fusion genes encoding a portion of HCF and the DNA binding domain of a transcription factor. Clones encoding HCF binding proteins provide for the complementation of the transcription factor and are identified through transcription of a reporter gene. See, e.g. Fields and Song (1989) Nature 340, 245–246 and Chien et al. (1991) Proc Natl Acad Sci USA 88, 9578–9582.

The invention also provides vectors comprising nucleic acids encoding HCF or HCF analogs. A large number of vectors, including plasmid and viral vectors, have been described for expression in a variety of eukaryotic and prokaryotic hosts. Advantageously, vectors may also include a promotor operably linked to the HCF encoding portion. The encoded HCF may be expressed by using any suitable vectors and host cells, using methods disclosed or cited herein or otherwise known to those skilled in the relevant art. The particular choice of vector/host is not critical to the invention.

Vectors will often include one or more replication systems for cloning or expression, one or more markers for selection in the host, e.g. antibiotic resistance, and one or more expression cassettes. The inserted HCF coding sequences may be synthesized, isolated from natural sources, prepared as hybrids, etc. Ligation of the coding sequences to the transcriptional regulatory sequences may be achieved by known methods. Suitable host cells may be transformed/transfected/infected by any suitable method including electroporation, $CaCl_2$ mediated DNA uptake, viral infection, microinjection, microprojectile, or other established methods.

Appropriate host cells include bacteria, archebacteria, fungi, especially yeast, and plant and animal cells, especially mammalian cells. Of particular interest are *E. coli*, *B. subtilis*, *Saccharomyces cerevisiae*, SF9 cells, C129 cells, 293 cells, Neurospora, and CHO, COS, HeLa cells and immortalized mammalian myeloid and lymphoid cell lines. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced HCF or HCF analogs.

Nucleic acids encoding HCF may also be introduced into cells by recombination events. For example, such a sequence can be microinjected into a cell, and thereby effect homologous recombination at the site of an endogenous gene encoding HCF, an analog or pseudogene thereof, or a sequence with substantial identity to an HCF-encoding gene. Other recombination-based methods such as nonhomologous recombinations, deletion of endogenous gene by homologous recombination, especially in pluripotent cells, etc., provide additional applications.

Experimental methods for cloning HCF, sequencing DNA encoding HCF, and expressing recombinant HCF are also set out in the working exemplification below. Other useful cloning, expression, and genetic manipulation techniques for practicing the inventions disclosed herein are known to those skilled in the art.

The compositions and methods disclosed herein may be used to effect gene therapy. See, e.g. Gutierrez et al. (1992) Lancet 339, 715–721. For example, cells are transfected with HCF sequences operably linked to gene regulatory sequences capable of effecting altered HCF expression or regulation. To modulate HCF translation, cells may be transfected with HCF complementary antisense polynucleotides.

One embodiment of antisense modulation employs HCF antisense sequences operably linked to gene regulatory sequences. Cells are transfected with a vector comprising an HCF sequence with a promoter sequence oriented such that transcription of the gene yields an antisense transcript capable of binding to HCF encoding mRNA. The HCF sequence of the vector is generally at least about 20 nucleotides, preferably at least about 50 nucleotides, more preferably at least about 200 nucleotides in length. Transcription of the "antisense gene" may be constitutive or inducible and the vector may provide for stable extrachromosomal maintenance or integration.

Alternatively, single-stranded antisense nucleic acid sequences, particularly DNA or deoxynucleotide analogs, that bind to genomic DNA or mRNA encoding at least a portion of HCF may be administered to the target cell at a concentration that results in a substantial reduction in HCF expression. In this embodiment, the antisense sequence is generally less than about 200 nucleotides, preferably less than about 50 nucleotides, more preferably less than about 20 nucleotides or longer in length. Alternatively, the sequence may be present as a ribozyme. The antisense sequences (including ribozymes) may be comprised of naturally occurring nucleotides, synthetic nucleotides, or combinations thereof. For example, the oxygen of the phosphate group may be replaced with sulfur, methyl, or the like.

For gene therapy involving the transfusion of HCF transfected cells, administration will depend on a number of variables that are ascertained empirically. For example, the number of cells will vary depending on the stability of the transfused cells, Transfusions media is typically a buffered saline solution or other pharmacologically acceptable solution. Similarly the amount of other administered compositions, e.g. transfected nucleic acid, protein, etc., will depend on the manner of administration, purpose of the therapy, and the like.

DRUG SCREENING AND AGENTS

The invention provides methods and compositions for identifying agents useful in modulating gene transcription, particularly genes containing the octamer element or the TAATGARAT motif. Such agents find use in the diagnosis or treatment of disease, particularly HSV infection.

Typically, prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. Examples of such modifications are disclosed herein.

Useful agents are identified with a range of assays employing HCF or HCF encoding nucleic acids. As examples, protein binding assays, nucleic acid binding assays and gel shift assays are useful approaches. More particularly, HCF is used in in vitro binding assays with either VP16 alone or with a combination or subcombination of VP16, Oct1 and TAATGARAT. HCF encoding nucleic acids are generally used in secondary assays, i.e. cell-based assays where HCF eDNA is introduced into cells with VP16, Oct1 and a reporter gene. The effect of prospective agents on VP16-HCF-dependent transcription is thereby determined.

Many appropriate assays are amenable to scaled-up, high throughput usage suitable for volume drug screening. Such screening will typically require the screening of at least about 10, preferably at least about 100, and more preferably at least about 1000 agents per week. Exemplary assays include assaying labeled VP16 binding to immobilized HCF, labeled HCF or HCF peptide binding immobilized VP16, etc.

A particular exemplary assay uses recombinant VP16 labelled with $^{32}$P by a heart muscle kinase. The TAATGARAT oligonucleotide is bound to a 96-well microtiter plate; a mixture of $^{32}$P-VP16, recombinant Oct1 and partially purified HCF is added; and the amount of $^{32}$P bound to the plate is then determined. In the presence of HCF the binding of $^{32}$P-VP16 is higher than background. The ratios of components are equivalent to those used in the gel shift assays described below. Agents disrupting HCF-VP16 binding are thereby detected.

Where the above described assays are not preferred, for example where a particular interface such as Oct1-VP16 or VP16-DNA is targeted, other useful assays are employed. For instance, an agent may interfere with the function of HCF but not with VP16-induced complex assembly (e.g. an antibody that binds to HCF but does not disrupt complex assembly would supershift the gel retardation complex and thus be detectable without disrupting the complex.) Other exemplary assays include HCF binding assays such as affinity chromatography, and gel retardation assays such as EMSA. Other examples of high throughput assays are disclosed herein or otherwise available through modifications of known methods using the disclosures herein.

Useful agents are typically those that bind to or disrupt the association of transcription associated factors. Preferred agents include those capable of modulating the expression of genes containing TAATGARAT or the octamer element, particularly those that disrupt HCF-VP16 binding. Useful agents may be found within numerous chemical classes, though typically they are organic compounds; preferably small organic compounds. Small organic compounds have a molecular weight of more than 50 yet less than about 2,500, preferably less than about 750, more preferably, less than about 250. Exemplary classes include peptides, saccharides, steroids, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Agents may be prepared in a variety of ways known to those skilled in the art. For example, peptides under about 60 amino acids can be readily synthesized today using conventional commercially available automatic synthesizers. Alternatively, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. If desired, the open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration of will generally be in the range of about 100 to 500 µg/ml in the dose administered. Other additives may be included, such as stabilizers, bactericides, etc. These additives will be present in conventional amounts. The following examples are offered by way of illustration and not by way of limitation.

EXAMPLES

EXPERIMENTAL PROCEDURES

Expression of GST-VP16ΔC and Oct-1 POU domain in *Esherichia coli*. VP16 (residues 5 to 411) lacking the carboxyl-terminal acidic activation domain was expressed as a glutathione-S-transferase (GST) fusion protein from the plasmid pETGSTVP16ΔC, which was constructed as follows: the VP16-coding sequence was excised from the plasmid pRIT2T. VP16ΔC wild type (Stem and Herr, 1991) as a 1.6-kb Sal I fragment and inserted into the Sal I site of a modified pUC119 polylinker (pBam/STOP) in which sequences between the Sal I and Hind III sites were changed so that the Xba I site of the polylinker is in frame to VP16 sequences beginning at the Sal I site and places an inframe termination codon followed by a Bam HI site downstream of the coding region. The VP16 sequences were transferred as an Xba I to Bam HI fragment to a modified version of pET11c.G.POU-1 (Aurora and Herr, 1991) in which a second Xba I site in the T7 promoter leader sequence had been destroyed.

Human Oct-1 POU domain was also expressed as a GST-fusion protein from the plasmid pET1 1c.G.POU-1 (Aurora and Herr, 1991).

GST-VP16ΔC and GST—Oct-1 POU fusion proteins were expressed in *E. coli* BL21 (DE3) cells and purified with glutathione-agarose essentially as described (Lai et al., 1992). The Oct-1 POU domain was separated from the GST moiety by thrombin cleavage and purified to 90% homogeneity by hydroxylapatite chromatography.

HCF assay conditions. HCF activity was measured by an electrophoretic mobility shift assay (EMSA). A 10-ml reaction contained 10 mM Tris-HCl (pH 7.9), 50 mM KCl, 1 mM dithiothreitol (DTT), 1 mM EDTA, 0.1% NP40, 1% glycerol, 2% Ficoll-400, calf thymus DNA (6.7 ng), poly d(IC) (1 mg), fetal bovine serum (FBS) (0.67 ml), recombinant Oct-1 POU domain (1 ng), recombinant GST-VP16 (40 ng), protein fraction containing HCF activity (0.1–1 ml), and a $^{32}$P-end-labeled DNA fragment (20,000 cpm) that contained the IE regulatory element from the HSV ICP0 gene [(ATGCTAAT)GATAT (SEQ ID NO: 04); termed (Octa$^+$)TAAT-GARAT]. After incubation at 30° C. for 30 min 1 ml of 30% glycerol was added, and samples were loaded onto a 4% acrylamide gel (3.9% acrylamide: 0.1% bis) in Tris pH 8.3 (200 mM), glycine (0.2M), and EDTA (1 mM). Glycerol (30%) plus bromophenol blue and xylene cyanol was added to the side lanes of the gel, and electrophoresis was continued until the bromophenol blue had migrated at least three-quarters of the distance down the gel. The gel was then dried for 45 min and subjected to autoradiography on Kodak XAR film at 4° C. with an intensifying screen (see FIG. 1).

Purification of HCF. HeLa S3 cells were grown in spinner flasks in Dulbecco's modified minimal essential medium (DMEM) supplemented with 5% FBS and harvested at a density of $10^6$/ml by centrifugation at 2500 rpm in a Sorvall H-6000A rotor for 15 min at 4° C. The cell pellet was washed with phosphate buffered saline (PBS), repelleted, snap-frozen in liquid nitrogen, and stored at −70° C. Extracts prepared from cells stored in this manner differed little in amount of HCF activity from extracts prepared from fresh cells.

All of the extract preparation and purification procedures were performed at 0° to 4° C. Buffers containing N-(2-hydroxyethyl)piperazine-N'-(2-ethanesulfonic acid) (HEPES) were prepared from a 1M stock that was adjusted to pH 7.9 at 4° C. with KOH. Dithiothreitol (DTT) was added fresh from a 1M stock and phenylmethylsulfonyl fluoride (PMSF) was added fresh from a 50 mg/ml stock in ethanol. Sodium metabisulfite was prepared as a fresh 1M stock in water 1 to 2 h before use. Benzamidine, sodium vanadate, and sodium fluoride were added fresh from 1.0M, 0.2M, and 50 mM stocks, respectively.

Frozen HeLa cell pellets were thawed rapidly in cold water and nuclear extracts prepared essentially as described (Dignam et al. (1983) Nucl Acids Res 11, 1475–1489). After dounce homogenization and centrifugation (30 min; 15,000 rpm, SS34 rotor), the supernatants were immediately incubated with wheat germ agglutinin—Sepharose (WGA) (Vector Labs, Burlingame) (5 ml of resin for every 12 l of cells) (Jackson and Tjian (1988) PNAS 86, 1781–1785) with rocking at 4° C. for 1 h. The resin had been equilibrated with buffer C [20 mM HEPES pH 7.9, 25% glycerol, 1.5 mM MgCl$_2$, 0.1 mM EDTA, 0.15 mg/ml DTT, 0.1% NP40, 0.2 mg/ml sodium metabisulfite, and 0.5 mM PMSF plus 0.42M NaCl. The protein-bound resin was then poured into a column, and protein was eluted with buffer C that contained 0.3M N-acetyl glucosamine (GlcNAc) and 50 mM NaCl. Fractions that contained protein as assessed by the Coomassie dye binding method (BioRad) were pooled and tested for HCF activity in an EMSA. Fractions containing HCF activity was pooled, and one of two purification schemes was carried out.

In one purification protocol, the WGA fractions that contained HCF activity were diluted with buffer C to 30 mM KCl and applied to an 8-ml Mono S FPLC column (Pharmacia). Protein was eluted with a 30 to 400 mM KCl gradient. Fractions were tested for HCF activity, which eluted at 150 mM. The HCF containing fractions were dialyzed against buffer C containing 50 mM KCl and loaded onto a 1-ml Mono Q FPLC column (Pharmacia). Protein was eluted with a 50 to 500 mM KCl gradient. Fractions that eluted between 200 and 500 mM KCl contained HCF activity.

In another purification protocol, the WGA fractions that contained HCF activity were pooled and loaded onto a 2-ml double-stranded DNA cellulose column (Sigma) pre-equilibrated in Buffer D supplemented with 0.05M KCl and developed with a 0.05M to 0.5M linear KCl gradient in buffer D. Fractions were assayed by EMSA with or without VP16 to monitor both HCF and endogenous Oct-1 activities. There was a small overlap in the elution points of these activities, and these fractions were excluded from further purification.

HCF-containing fractions were pooled, adjusted to 0.1M KCl, mixed with GST-VP16ΔC beads, and rotated end-over-end for 30 min at 4° C. All manipulations were performed in the absence of DTT. The GST-VP16ΔC fusion protein was synthesized in *E. coli* as described above. Approximately 0.5 mg of GST-VP16DC were bound per ml of swollen glutathione-agarose beads. The bead slurry was poured into a EconoPat column and washed with buffer D supplemented with 0.1M KCl. The column was then washed with 5 column volumes of buffer D containing 0.3M KCl, which was followed by a wash with 5 column volumes of buffer D containing 1.0M KCl.

The 0.3M fractions were dialyzed against 10 mM Hepes-KOH pH7.6, 0.05M KCl, 10% glycerol, 1 mM DTT, 0.5 mM PMSF and concentrated on a 1-ml Mono Q column equilibrated in the same buffer. The column was washed with load buffer and eluted with a linear 0.05 to 0.5M KCl gradient. Activity eluted at approximately 150 mM KCl. The fractions with peak activity were pooled and gently layered (200 to 250 ml per gradient) onto a 2-ml 15 to 35% glycerol gradient prepared in 10 mM Hepes-KOH pH7.9, 0.1M KCl, 0.1% NP40, 1 mM DTT, 0.5 mM PMSF. The gradients were centrifuged at 4° C. for 18 h at 39,000 rpm in a SW55 Ti (Beckman) rotor. Fractions (approximately 200 ml) were collected as drops from the bottom of the gradient. Molecular weight markers of known sedimentation coefficients (Boehringer Mannheim) were applied to a parallel gradient and assayed by SDS polyacrylamide (12%) gel electrophoresis (SDS PAGE) and Coomassie Blue staining.

Preparation of whole cell extracts. *Spodoptera frugiperda* Sf9 cells were obtained from B. Stillman and maintained in semi-suspension at 27° C. in TNM-FH medium (Gibco) plus 10

FBS. Drosophila Schneider line 2 (SL2) cells were grown in spinner culture (250 ml) in M3 media (Gibco) supplemented with 10% heat-denatured FBS. Cells were collected by centrifugation, washed in PBS and lysed in buffer D with 0.42M KCl and 0.5% NP40 at 4° C. Lysates were rotated for 30 min and the nuclei and cellular debris removed by centrifugation at 10,000×g. Extracts were snap frozen in liquid nitrogen and stored at −70° C. Generation and sequencing of HCF peptides. Mono Q—purified HCF fractions and glycerol gradient fractions containing about 500 ug of total protein were precipitated with one-fourth volume of 100% trichloroacetic acid (TCA) plus 4 mg/ml sodium deoxycholate. Protein pellets were acetone washed, resuspended in SDS sample buffer containing saturating amounts of urea, heated at 65° C. for 5 min, and subjected to SDS PAGE on a 7% acrylamide gel. A sample (15-ml) of the protein fraction was taken prior, to TCA precipitation and subjected in parallel to SDS polyacrylamide gel electrophoresis, and this lane of the gel was subsequently silver-stained. The polypeptides on the rest of the gel were electrophoretically transferred in 192 mM glycine, 25 mM Tris base, and 0.01% SDS to a polyvinylidene difluoride (PVDF) membrane, and the membrane was stained with 0.1% Ponceau S in 0.1% acetic acid to visualize the transfered proteins. Protein bands were excised as indicated (FIG. 2) and treated with either trypsin or endoproteinase Lys-C exactly as described in Fernandez et. al. (1992) Analytical Biochem 201, 255–264. The resulting peptides were separated by chromatography on an Applied Biosystems (ABI) RP-300 C8 column (1×250 mm, 300 A) with an ABI 130 HPLC. Chromatographic conditions were as follows: solvent A=0.1% trifluoroacetic acid (TFA), B=0.085% TFA, 90% acetonitrile; gradient=2 to 60% B over 60 min, with a flow rate of 75 ml/min. Peptide elution was monitored by absorbance at 216 nm, and peak protein fractions were collected manually and immediately frozen on dry ice. Identical elution profiles were obtained for peptides generated from the 150-kD, 120-kD, and 110-kD proteins. Peptide fractions were subjected to sequence analysis on an ABI 477A with a 120A analyzer. The conditions used were the ABI FAST-1 reaction and conversion cycles, and FAST gradient on the analyzer.

Screening of lgt10 libraries for cDNAs encoding HCF. Oligonucleotide guessmer probes were designed on the basis of peptide sequences obtained from purified HCF as described above and are indicated in FIG. 3. The guessmer probes were end-labeled with g-$^{32}$P-ATP and T4 polynucleotide kinase and used to screen two lgt10 cDNA libraries, one from human hepatoma cells and one from human platelets. Bacteriophage-infected XL1 Blue *E. coli* were plated on LB agar plates and the plates were overlayed with nitrocellulose filters, and individual filters were screened in duplicate with a mixture of guessmer probes. After lifting the filters from the plate they were denatured for 2 min, neutralized for 5 min, and washed twice in 2×SSC for 5 min at room temperature (Sambrook et al., supra) Filters were rinsed in chloroform, blotted on 3MM paper, and baked at 80° C. for 2 h. Baked filters were then prehybridized in 6×SSC and 10× Denhardt's solution (Sambrook et al., supra) for 2 hours at 42° C. The $^{32}$P-labeled probes were boiled and added to hybridization buffer (1M NaCl, 50 mM Tris pH 7.4, 2 mM EDTA, 10×Denhardt's, 0.5% SDS, and 70 mg/ml salmon sperm DNA).

Prehybridized filters were transferred to the hybridization buffer containing the probe and were incubated for 12 to 16 hours at 42° C. Filters were then washed in buffer 1 [1M NaCl, 50 mM Tris (pH 8.6), 2 mM EDTA, 1% SDS) (with 2 changes of buffer), buffer 2 (0.5M NaCl, 25 mM sodium phosphate pH 6.5, 0.5% SDS), and buffer 3 (0.5M NaCl, 50 mM sodium phosphate pH 8.5, 2 mM EDTA, 0.5% SDS), each for 2 hours at 55° C. Filters were then subjected to autoradiography. Rescreened plaques that were scored as positive on duplicate filters were isolated, replated on LB agarose plates, and rescreened with each of three guessmer probes individually. Plaques that were scored as positive with two or more probes were plaque purified. These included phages H3, H12, and P5, with H and P representing plaques isolated from the hepatoma and platelet libraries, respectively. All three of the clones bound to guessmer probes 1 and 2. Phage DNA was isolated, and the inserts were excised by restriction digestion. All phage eDNA clones were subcloned into the polykinkers of pBluescript II KS+ or SK+ (Stratagene) or the filamentous phage M13mp13. Sequencing reactions were performed according to the Sequenase version 2.0 DNA sequencing Kit manual (US Biochemicals) with oligonucleotide primers and denatured double-stranded plasmid DNA templates or single-stranded M13 DNA.

The deduced amino acid sequence of H12 contained the deduced amino acid sequences of guessmer probes 1 and 2, as well as the amino acid sequence of peptide 32. Additional clones were obtained by multiple screenings of a polydT-primed human teratocarcinoma NTera-2D 1 cell lgt10 cDNA library (Skowronski et al., 1988, Mol Cell Biol 8, 1385–1397), a polydT-primed Hela cell lgt10 cDNA library, and a random-primed primed HeLa lgt10 cDNA library. Probes were gel-purified restriction fragments labeled by random priming (Amersham Multiprime DNA labeling system) or overlapping 30-base oligonucleotides labeled by 5′ to 3′ repair with Klenow fragment (Sambrook, et al., supra). The restriction fragments were prehybridized (1 to 2 h) and hybridized (16 h, 60° C.) in 6×SSC, 5×Denhardt's solution, 0.2% SDS, and 100 mg/ml denatured salmon sperm DNA. Filters were washed twice in 2×SSC, 0.5% SDS at 60° C. for 30 min, and then three times in 0.2×SSC, 0.1% SDS at 60° C. for 30 min. Positive phage were plaque purified and phage DNA isolated by a CTAB method (Manfioletti and Schneider, 1988, Nucl Acids Res 16, 2873–2884) or with PhageSorb matrix (Promega).

Generation of recombinant H12 fusion protein and production of antibodies. The H12 sequence was excised from BlueScript KS+ by digestion with Eco RI and inserted in-frame into the EcoRI site of an *E. coli* expression vector TYP-7) that is based on the T7 expression system. The resultant plasmid CYP7-H12) was used to transform *E. coli* strain HMS 174 (DE3). The cells were then grown at 37° C. in terrific broth (Sambrook et al. supra) plus 50 ug/ml ampicillin to an optical density of 1.0 at 600 nm, and then induced for 2.5 hours with isopropyl b-D-thiogalactoside (IPTG) at a final concentration of 0.25 mg/ml. The bacterial pellets were harvested by centrifugation and resuspended in solution A [10 mM Tris-HCl (pH 7.9); 25% sucrose; 100 mM KCl; 2 mM DTF; 2 mM PMSF; 2 mM sodium metabisulfite). Solution B (300 mM Tris-HCl, pH 7.9; 100 ; mM EDTA; 4 mg/ml lysozyme) was added, and extracts were incubated for 10 min on ice. Solution C (1M LiCI; 20 mM EDTA; 0.5% NP 40) was added to the bacterial suspension, which was then sonicated on ice with three 10-s pulses at a setting of 5 (Branson). The inclusion bodies containing the H12 fusion protein were pelleted by centrifugation and washed once with solution D (10 mM Tris-HCl, pH 7.9; 0.1 mM EDTA; 0.5M LiCl; 0.5% NP 40; 1 mM DTT; 1 mM PMSF; 1 mM sodium metabisulfite) and twice with solution E (same as solution D except without the LiCl). The pellets were disrupted by sonication at each wash step. SDS sample buffer was added, and the pellets were heated at 100° C. for 5 min and subjected to electrophoresis on an SDS polyacrylamide (7%) gel. Approximately 80% of the protein in the final pelleted fraction was the H12 fusion protein, which was judged to be approximately 80 kD. The identity of the recombinant protein was confirmed by amino acid sequencing of tryptic peptides by the methods described above.

A comparable preparation of H12 fusion protein was produced, and the final pelleted fraction was resuspended in 20 mM Tris-HCl (pH 7.9), 50 mM KCl, 1 mM EDTA, 10 mM $MgCl_2$, 20% glycerol, 1 mM DTr. The H12 fusion protein was solubilized by addition of NaOH to a final concentration of 50 mM and heating to 65° C. for 10 min. The preparation was then neutralized by addition of Tris-HCl (pH 7.5) M and HCl to 50 mM, leaving approximately 80 to 90% in the soluble fraction. This preparation was used for production of antibodies to recombinant H12 in mice and rabbits. Antibodies were produced by Berkeley Antibody Company (BAbCO) with the use of standard procedures.

Detection of HCF in variously processed HeLa extracts with antibodies to native and recombinant H12 by immunoblotting. HeLa nuclear extracts and WGA preparations were prepared as described above. For whole-cell HeLa extracts, cells were grown on 100-mm plates in DMEM supplemented with 10% FBS and pennicillin-streptomycin, washed with PBS, and lyced in 1 ml of SDS sample buffer (5×) without bromophenol blue. The lysed cells were scraped from the plate, transferred to a microfuge tube, sonicated with a microtip at setting 2 for two 5-s pulses, and centrifuged at 12,000g for 2 min. SDS sample buffer (5×) containing bromophenol blue was added to all extracts, and samples were subjected to electrophoresis on an SDS poly-acrylamide (7%) gel. Proteins were transferred to nitrocellulose (transfer buffer, pH 8.3: 192 mM glycine, 25 mM Tris base, 0.01% SDS), and immunoblotting was performed as described (Sambrook et al., supra). Antisera to native HCF and H12 were used at a 1:200 dilution, and immunoreactive proteins were visualized by the alkaline phosphatase method (Sambrook et al., supra).

Disruption of the VP16-induced complex by addition of antibodies to recombinant H12 fusion protein. The EMSA was performed with a WGA fraction as the source of HCF essentially as described above, except that preimmune sera and various dilutions of immune sera (diluted with preimmune sen) were incubated with protein extracts for 15 min at room temperature prior to addition of the remainder of the assay reagents.

Co-immune precipitation of a VP16-HCF complex from HeLa cell extracts. HeLa cells were grown on 100-mm plates in DMEM plus 10% FBS. For production of cell extracts, the culture medium was removed, and cells were washed with ice-cold PBS, incubated on ice for 30 min in lysis buffer (250 mM NaCl, 0.1% NP40, 50 mM HEPES pH 7.9), transfered to a microfuge tube, and centrifuged for 2 min to remove cell debris. Preclearing of the lysate was accomplished by incubation of extracts with 50 ml of preimmune serum for 60 min at 0° C. and then with a 50-ml pellet of formalin-fixed Staphylococcus A cells for 30 min at 0° C. Extracts were then centrifuged at 12,000g for 5 min to remove the Staph A cells. Ascites containing an antibody to VP16 (LP1; 5 ml per 106HeLa cells, McLean et at., (1982) J Gen Virol 63:297–305) was added to the supernatant, which was then incubated at 0° C. for 1 h. To harvest the immune complexes protein A—Sepharose (Sigma; 100 ml of a 10% slurry) was added, and lysates were incubated at 4° C. with agitation. Protein-A beads carrying the immune complexes were collected by centrifugation at 4° C. in a microfuge for 20 sec at 10,000 g and washed three times with lysis buffer. After the final wash, SDS sample buffer was added, and the beads were heated to 100° C. for 5 min and pelleted by centrifugation. The protein-containing supernatants were subjected to SDS PAGE on a 7% gel, and coprecipitiating HCF polypeptides were detected by immunoblotting with antibodies to recombinant HCF and visualized with $^{125}I$-labeled protein A.

For infection with HSV-1, HeLa cells were treated with cycloheximide (0.1 mg/ml in DMEM with 10% serum) for 30 min and then either mock-infected or infected with HSV-1 (multiplicity of infection=5) in DMEM with 2% serum and cycloheximide (mock-infected cells were treated in an identical manner except that addition of virus was omitted). After 1 h, the virus-containing medium was aspirated, and cells were washed with DMEM plus cycloheximide and incubated at 37° C. for 2 to 3 hours in DMEM plus 10% serum and cycloheximide. Extracts were produced and immune precipitation and immunoblotting were carried out as described above for the VP16-supplemented HeLa extracts.

HCF ACTIVITY IS CONSERVED BETWEEN MAMMALS AND INSECTS.

Figure 1:
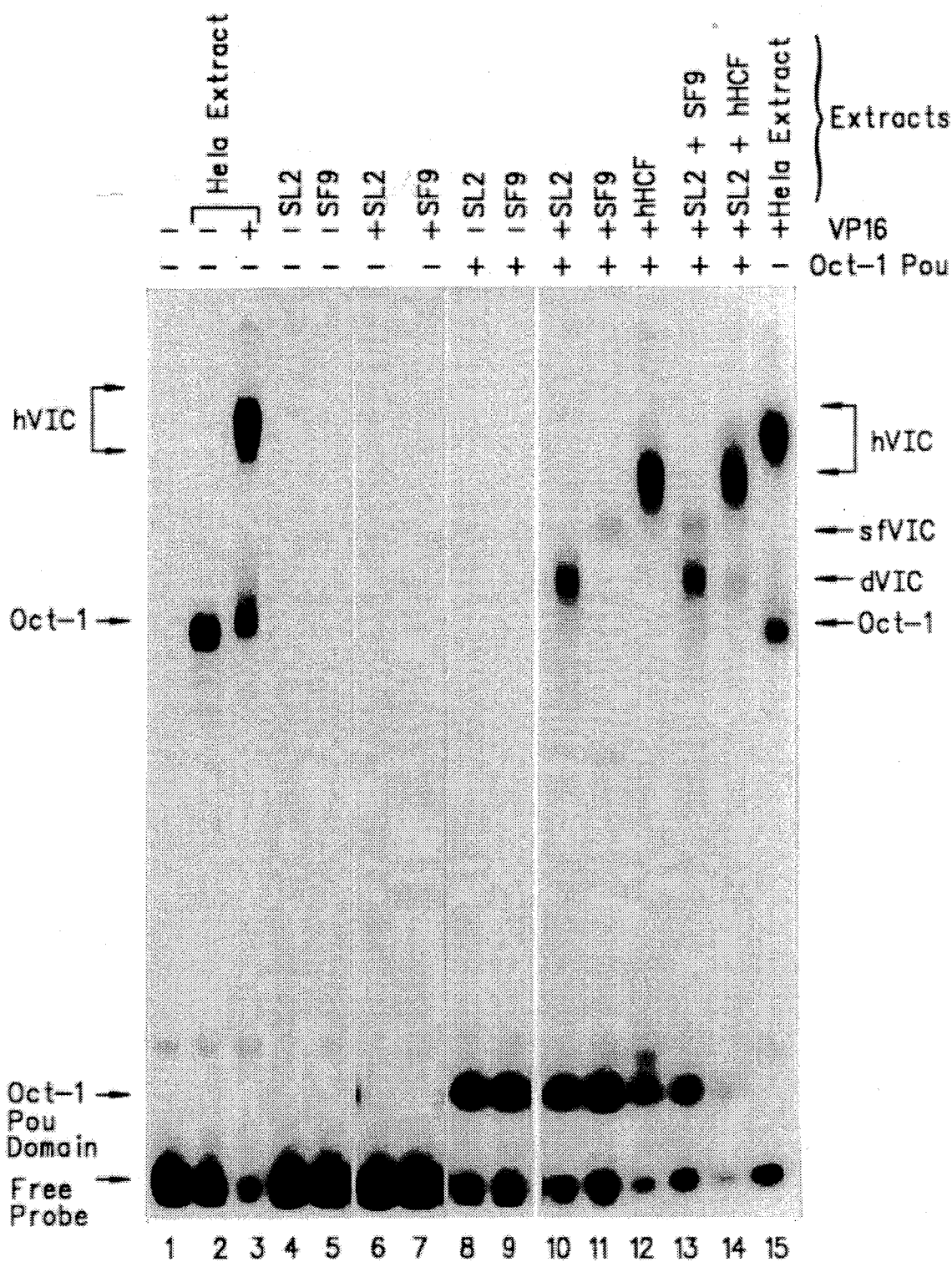
FIG. 1 Drosophila, Spodoptera, and human HCF give rise to VP16-induced complexes of different mobility. Whole cell exctract from Drosophila SL2 cells and Spodoptera Sf9 cells were tested for HCF activity by gel mobility-shift assay. Labelled (octa+)TAATGARAT probe was incubated on its own (lane1), with HeLa nuclear extract (lane 2) or with HeLa nuclear extract and VP16 (lane3) to indicate the relative mobilities of the unbound probe and the VP16-induced complex. Drosophila and Spodoptera extracts were assayed pairwise in lanes 4 to 11, on their own (lanes 4 and 5), with recombinant human Oct-1 POU (lanes 6 and 7), with GST–VP16 (lanes 8 and 9) or with both Oct-1 POU domain and GST-VP16 (lanes 10 and 11). In lane 12 partially purified human HCF, which is devoid in Oct-1 activity, was incubated with both Oct-1 POU domain and GST-VP16. The Drosophila extract was mixed with the Spodoptera extract (lane 13) or human HCF (lane 14) and incubated for 10 mins at 30° C. and prior to assembly of gel-mobility shift reactions that included Oct-1 POU domain and GST-VP16.

HCF has been characterized in part by EMSAs. When nuclear extracts from mammalian cells are incubated with a probe containing the (Octa$^+$)TAATGARAT motif from the herpes virus ICP0 gene promoter a single protein-DNA complex is observed that corresponds to binding of the cellular factor Oct-1 (FIG. 1, compare lanes 1 and 2). If VP16 is included in the reaction a second, more slowly migrating complex is observed (lane 3). Several studies have shown that this VP16-induced complex (VIC) consists of Oct-1, VP16, and one or more additional factors termed HCF. HCF activity has also been identified in insect cells (Kristie et al., 1988). When whole cell extracts from the *Drosophila melanogaster* SL2 cell line or the fall army worm *Spodoptera frugiperda* Sf9 cell line were incubated with the (Octa+)TAATGARAT probe, recombinant human Oct-1 POU domain and VP16, a novel complex was detected (lanes 10 and 11). Formation of this complex was dependent on the addition of both VP16 and Oct-1 POU domain, as no specific complexes were observed if the extracts were incubated with the probe alone (lanes 4 and 5) or mixed individually with the Oct-1 POU (lanes 6 and 7) or with VP16 (lanes 8 and 9). The VIC formed with partially purified human HCF (see below) is also shown (lane 12). A striking feature was the distinctive mobilities of the VP16-induced complexes incorporating HCF from the different organisms. Under our assay conditions and in contrast to previous reports, HCF from Sf9 cells yielded a faster migrating complex than did HCF from human HeLa cells.

Little has been published about the stoichometry of the VIC. In particular, the nature of HCF has not been charaterized nor has not been known whether HCF corresponds to one or several factors. A convenient assay for monitoring the oligomerization state of DNA binding proteins has been to mix full-length and truncated forms of the protein, and then determine by EMSA whether heteromeric complexes of novel mobility can be generated (Hope & Struhl). As a variation of this tehnique, we mixed HCF obtained from different organisms to ask whether multiple HCF factors are incorporated into the VP16-induced complex. When the Drosophila extract was mixed with the Spodoptera extract (lane 13) or human HCF (lane 14) additional (intermediary) complexes were not detected. These results may suggest that there is only a single HCF factor in each VIC. However, they do not exclude the possibility that HCF activity comprises multiple components, and either the subunits cannot be mixed across organisms or the complex is particularly stable. In any case, these results indicated that HCF is a well-conserved activity.

PURIFICATION OF HUMAN HCF

One method of isolating cDNA clones that encode proteins identified by a particular function is by obtaining peptide sequence from the purified proteins, which is used to derive oligonucleotide probes for screening cDNA libraries. With respect to HCF, the our data suggested to us a number of advantages to this approach. First, the number of polypeptides and/or other compounds needed to reconstitute HCF activity was not known. The extemely slow relative mobility of the VIC, the sensitivity of HCF to inactivation by heat and chemical denaturation all suggested that HCF activity consisted of a multisubunit complex. If this were the case, a cloning strategy based on bacterial expression or phage display would be unlikely to succed. Secondly, the identity of any isolated cDNA clones could be confirmed directly by comparison of the predicted amino acid sequence with the actual peptide sequence, an important criteria if the identifying function could not be regenerated from individual cDNAs.

We purified HCF from HeLa cells to near homogeneity using two related schemes (see Experimental Procedures). The procedure outlined in detail below used a combination of affinity and conventional chromatograpic steps plus glycerol gradient sedimentation (also see FIG. 2). HCF activity was monitored by EMSAs using recombinant Oct-1 POU and GST-VP16ΔC and could be correlated throughout the purification with a set of at least eight polypeptides that ranged in apparant molecular weight from 110 to 300 kD.

Preliminary studies showed that HCF, like certain other nuclear regulatory proteins, is modified with multiple N-acetyl glucosamine (GlcNAc) sugar residues and can be bound to wheat germ agglutinin (WGA) beads. Because the majority of promins (>99%) in a typical nuclear extract are not retained by lectin columns (Jackson and Tjian, 1989), WGA affinity chromatography used as an initial purification step gave substantial enrichment of HCF activity. By mixing fresh nuclear extracts with WGA agarose beads at a high salt concentration (0.42M) and 0.5% NP40, we could routinely bind and then recover by competition with the free GlcNAc, about 80 to 90% of HCF activity. This single step gave a 200-fold purification. Use of a fresh extract was critical, as a significant fraction of active HCF (up to 60%) failed to bind to the WGA affinity column if the crude nuclear extract had been frozen or dialysed. We suspect that this is because of deglycosylase activities in the extract that remove or modify enough sugar residues to substantially reduce the affinity of HCF for WGA.

A sizable proportion of Oct-1 (40–50%) is also glycosylated (Pierani et al., 1990, Mol Cell Biol 10, 6204) and copurified with HCF. This contaminating Oct-1 complicated quantitation of HCF activity in subsequent steps because the endogenous native Oct-1 appeared to be incorporated into the VIC more efficiently than recombinant Oct-1 POU. It had been shown that, although both HCF and Oct-1 bind to double-stranded DNA-cellulose, the two activities could be differentially eluted with a salt gradient (Katan et al., 1989). Therefore, after HCF was eluted from the WGA column, the peak protein fractions were loaded directly onto a DNA-celluose column preequilibrated with buffer D containing 50 mM KCl, and the column developed with a linear KCl gradient (0.05 to 0.5M). HCF eluted early in the gradient (between 75 and 100 mM KCl), while Oct-1 eluted at a higher salt concentration (>180 mM). This chromatographic step gave a further 50-fold purification and removed many DNA-binding proteins that required higher salt concentration for elution.

Figure 2A:
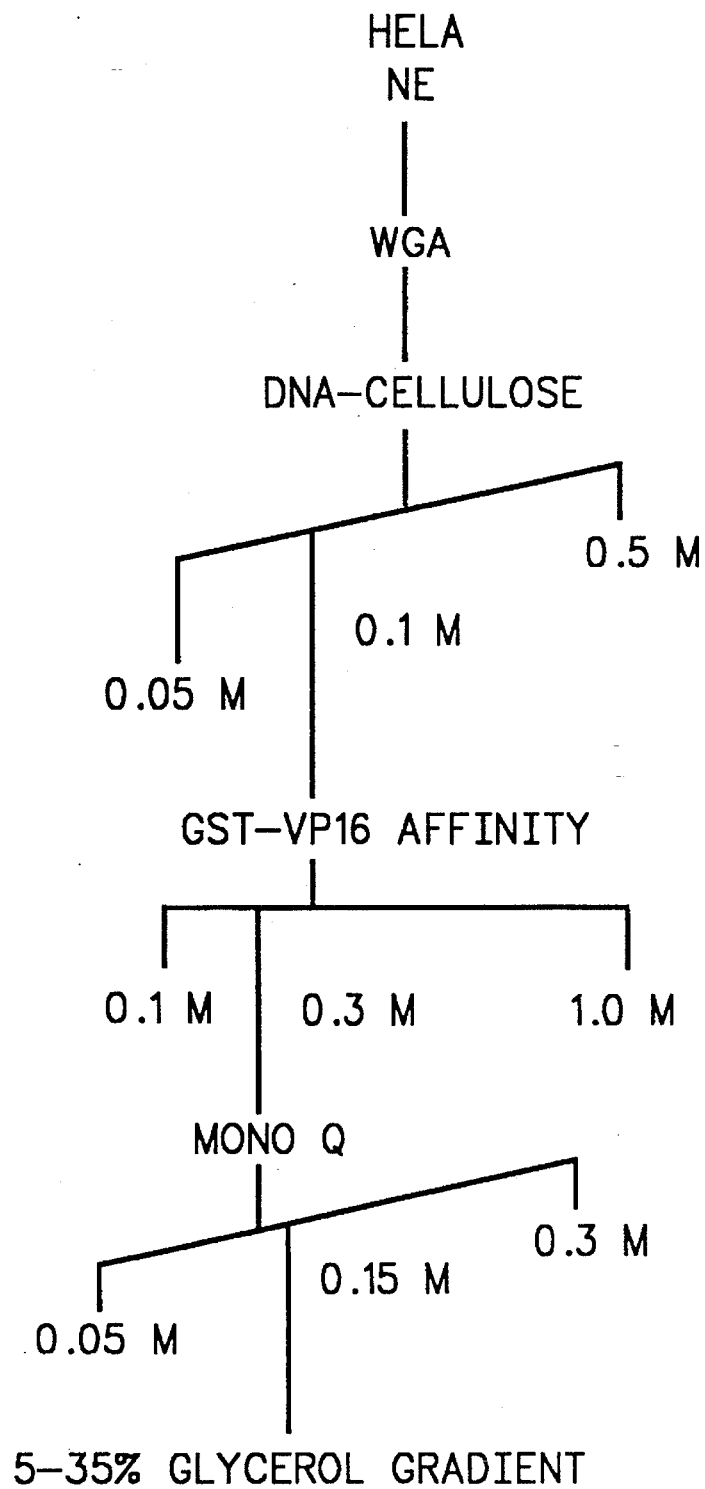
FIG. 2. Purification of human HCF.
Figure 2B:
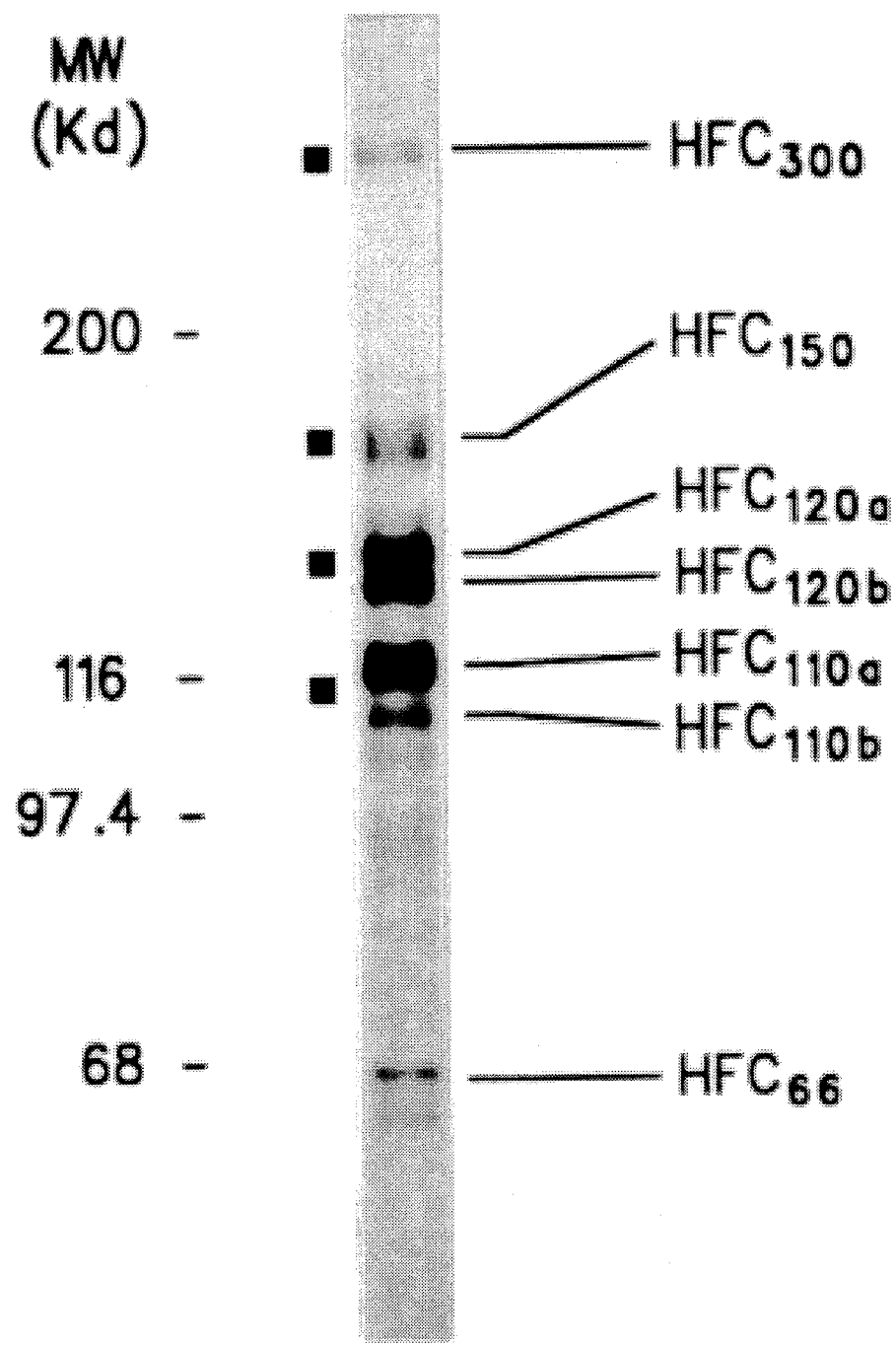
Figures 2C, 2D:
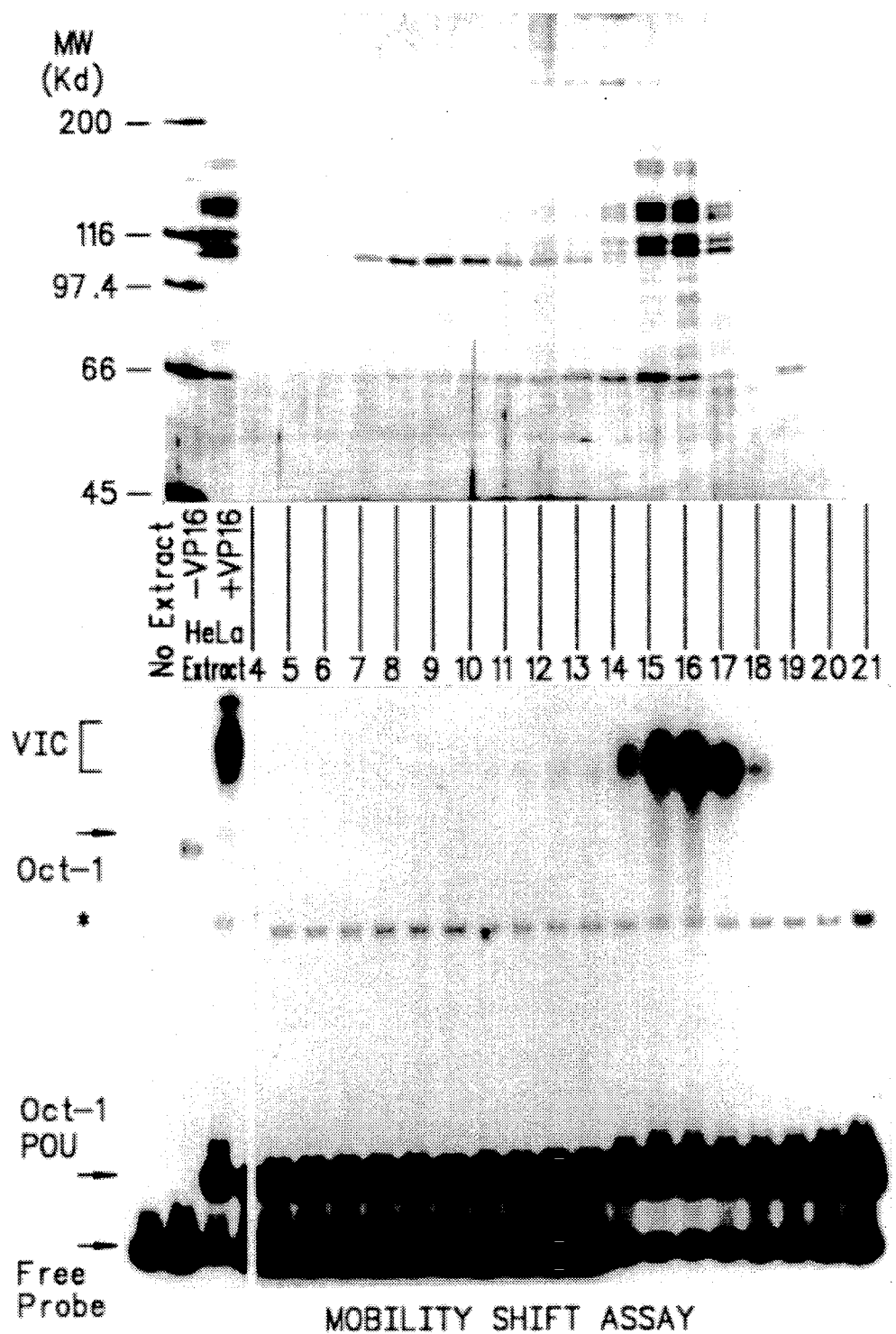

A notable feature of HCF is its ability to complex with VP16 independently of Oct-1 or specific DNA. This allowed us to use an affinity resin that had GST-VP16ΔC bound to glutathione-agarose beads in the purification of HCF. The background of nonspecifically bound protein was lower with the GST system than with either VP16 covalently linked to activated Sepharose beads or with a VP16-protein A fusion bound to IgG-agarose beads. The peak HCF-containing fractions from the DNA-cellulose column were pooled, adjusted to 100 mM KCl, and mixed batch-wise with GST-VP16ΔC-loaded glutathione agarose beads. The beads were then poured into a column and washed, and HCF was eluted with 300 mM KCl. GST-VP16ΔC remained bound to the beads under these conditions and could not be detected in the eluate by EMSA. SDS PAGE and subsequent silver-staining of the eluted proteins revealed a patten that was nearly identical to that shown in FIG. 2B. Fractions that contained HCF activity were pooled and concentrated with the use of Mono Q HPLC, which also removed some minor contaminants, and then subjected to glycerol gradient sedimentation. Proteins in the gradient fractions that were separated by SDS PAGE and silver-stained are shown in FIG. 2, panel C, while panel D shows the same fractions assayed for HCF activity by EMSA. HCF activity peaked in fractions 14 to 17 and correlated with a series of polypeptides clustered at 150 kD, 120 kD and 110 kD. Although the 300-kD polypeptide peaked in fractions 14 and 15, very little was detected in the most active fractions (16 and 17). The 66-kD polypeptide was probably a breakdown product, as its relative abundance varied among preparations. The major polypeptide of approximately 110 kD did not cosediment with activity and thus appeared to be a contaminant.

On the basis of protein standards applied to a parallel gradient, we estimated a sedimentation coefficient for HCF of approximately 5S. The purified HCF was also subjected to gel filtration chromatography and based on elution time was estimated to have a molecular weight of 450 to 650 KD.

We obtained a polypeptide profile similar to that provided by the glycerol gradient by subjecting WGA-purified HCF to chromatography first on a Mono S column and then on a Mono Q column (see Experimental Procedures). These three purification steps yielded proteins of 300, 150, 120, and 110 kD. Because the same pattern of polypeptides copurified through a collection of diverse chromatographic steps, we believed that most of the major polypeptides were related to HCF activity. In fact, this distinctive banding pattern was apparant in the peak activity fractions after DNA-cellulose chromatography. We therefore decided to obtain amino acid sequence from each of the observed polypeptides.

SEQUENCING OF PEPTIDES DERIVED FROM PUTATIVE HCF POLYPEPTIDES

Proteins in the most purified HCF fractions were separated by SDS PAGE and transferred to a PVDF membrane. Individual protein bands were excised after staining the membrane with Ponceau S and digested in situ with either trypsin or lys-c. The resulting peptides were separated by HPLC, and selected peptides were sequenced by Edman degradation. Protein bands in the HCF sample used for lys-c digestion were sufficiently well resolved so that the bands corresponding to the two major polypeptides from the 120 kD and 110 kD clusters (termed p120a, p120b, p110a, and p110b respectively, see FIG. 2B) could be isolated individually. The HPLC profiles of lys-c—generated peptides from the 150 kD doublet, p120a, p120b, and p110a were extremely similar, suggesting that the parent polypeptides were closely related. Although the peptide profile for p110b was more complex, there still appeared to be many peaks in common with the previous profiles. We suspect that the extra peptides were derived from the contaminating 110 kD polypeptide that did not correlate with activity after glycerol gradient sedimentation (see FIG. 2C). Only a small amount of the 300-kD polypeptide was able to be transferred to the PVDF membrane, probably owing to its large size, and thus gave insufficient peptide yields for amino acid determination. Direct amino-terminal sequencing was also unsuccessful probably as a result of modification of the terminus.

To confirm that the p150, p120a, p120b, p110a, and p110b polypeptides were related to each other as suggested by their similar HPLC profiles, we selected two well resolved peaks that appeared to be common to each digestion. The deduced amino acid sequences (FIG. 3) were identical in nearly every case, and differed only at ambiguous residues. This argues strongly that the majority of these polypeptides are encoded by the same gene and that the protein heterogeneity is generated at the level of mRNA processing or post-translational modification. Sixteen additional peptide sequences were also obtained.

ISOLATION OF cDNAS THAT ENCODE HCF

Using the peptide sequence obtained from the purified protein, we designed three guessmer probes and used them to screen a human hepatocyte and a human platelet cDNA library. Three recombinant bacteriophages (1H-3, 1H-12, and 1P-5) gave positive signals when hybridized with two of the three guessmers. The inserts of recombinants H-3 and H-12 were cloned and sequenced and found to contain overlapping open reading frames. Inspection of the deduced amino acid sequence revealed the peptide sequences corresponding to the two hybridizing guessmers. In addition, the ORF encoded a third peptide sequence that we had obtained from the purified HCF protein, but had not been used to design a guessmer for library screening. These results suggest that these cDNA inserts were derived from the gene encoding the protein we had purified and sequenced.

The H-3 insert was then used as a probe to screen additional cDNA libraries at high stringency. Multiple overlapping clones were isolated that together gave a composite cDNA of about 5.3 kb. The ORF was terminated by a nonsense codon (UGA) ten amino acids downstream of pep-12, but remained open upstream. Because Northern (RNA) blot analysis with total HeLa RNA detected a single 9.5 to 10 kb transcript and many peptide sequences remained unaccounted for, we extended the composite cDNA by repeated rounds of screening with probes derived from the 5' most sequences after each round. A weak polyadenylation signal (5" AAUUAAAA3') was found 1791 bp downstream of the 3' end of the ORF and was followed 12 bp later by a stretch of 15 A's, presumably part of the polyA tail. No other cDNAs further extended the 3' end, suggesting that this was the bona fide 3' end of the transcript. Southern Blotting analysis of human DNA at reduced stringency indicated that the eDNA is derived from a single copy gene.

Sixteen other peptide sequences were encountered (see FIG. 2). The complete ORF is notably GC-rich. A number of functionally significant features are apparent from the disclosed amino acid sequence of HCF (SEQ ID NO: 05). For example, shown boxed in FIG. 3c are 8 copies of a 26 amino acid repeat sequence: (SEQ ID NO: 06), (SEQ ID NO: 07), (SEQ ID NO: 08), (SEQ ID NO: 09), (SEQ ID NO: 10), (SEQ ID NO: 11), (SEQ ID NO: 12), (SEQ ID NO: 13), and (SEQ ID NO: 14), respectively. "THE TNT" consensus sequence (SEQ ID NO: 15) also shown in FIG. 3e. The 2 cysteines and 1 histidine in each repeat define a metal binding domain. This structure presents a target for compounds which specifically disrupt protein-protein interaction domain or a protein-DNA interface. By disrupting the interaction between repeats of HCF and VP16, Oct1 or DNA, such counpounds could inhibit VP16 function and form the basis of a drug against HSV.

The position of the repeat sequences within HCF indicates that they are the recognition motif for a site-specific protease, and that their scission produces the spectrum of HCF polypeptides observed in the cell. These repeat sequences have not been described in any known protein and thus represent the progenitor of a new family of site-specific protease recognition sites. Accordingly, such sequences are usefully incorporated into other proteins to achieve a novel site-specific cleavage, e.g. one that converts a pro drug into a drug or inactivates an existing drug.

Other apparent structural regions within the HCF sequence include: clusters of the bulky hydrophobic residues tryptophan, phenylalanine and tyrosine from amino acids 19–384 & 1812–1999; clusters of the basic residues lysine and arginine from amino acids 426–875; clusters of the acidic residues aspartic acid and glutamic acid from amino acids 1445–1753; and a strongly alpha helical region from amino acids 1609–1647. These regions constitute targets for disruption of protein-protein or protein-DNA interactions including those with VP16 and Oct1.

ALTERATION OF VIC FORMATION BY ANTIBODIES TO NATIVE AND RECOMBINANT HCF

As a means of deciphering whether the cDNA we isolated encoded a protein related to the HCF in the VIC, we sought to obtain antibodies to a fragment of the cDNA-encoded recombinant protein and test whether they disrupted or altered the mobility of the VIC. The H-12 cDNA insert was subcloned into a plasmid vector for expression of the encoded protein in *E. coli*. A recombinant protein of approximately 80 kD was produced, isolated from inclusion bodies, and injected into animals for antibody production. EMSAs were performed whereby various dilutions of pre-immune and immune sera were incubated with a WGA fraction containing HCF activity prior to addition of the assay reagents (FIG. 4). As a comparison, antiserum raised against HCF purified from HeLa nuclei was also tested, along with a monoclonal antibody to VP16 and a control antibody. Antibodies to purified HCF disrupted VIC formation at high concentrations and altered its mobility at lower concentrations, while preimmune serum had no effect, indicating that the most purified protein fraction contained HCF. Antibodies to recombinant HCF disrupted the VIC at dilutions of 1:10, 1:100, and 1:500. The 1:5000 dilution only slightly shifted the VIC, as did the preimmune serum. These results indicate that the isolated eDNA encodes at least a component of HCF.

RECOGNITION OF MULTIPLE FORMS OF HCF BY ANTIBODIES TO RECOMBINANT HCF

Purification of HCF from HeLa nuclei yielded a collection of protein products, at least some of which contained related peptides (FIG. 3). However, we had been unable to obtain amino acid sequence from the largest (300 kD) polypeptide and were therefore unable to determines its relatedness to the lower molecular weight components. As a means of determining which of the purified species were related to recombinant HCF we performed immunoblots with variously processed HeLa cell extracts.

As seen in FIG. 5, antisera to both native and recombinant HCF recognized *E. coli*-produced recombinant HCF (H-12), the 300-kD protein in HeLa nuclear extracts and WGA extracts, and the three groups of proteins at the 150-, 120-, and 110-kD regions of the gel.

These results indicated that the 300-kD protein was related to the recombinant HCF as well as to a number of the lower molecular weight HCF species. However, it was still unclear as to whether the multiple HCF components were produced in vivo and thus possibly functionally relevant, or whether their generation was an artifact of our purification protocol. Therefore, we grew HeLa cells in culture, and lyced them directly in SDS sample buffer; the extracts were subjected to electrophoresis on an SDS polyacrylamide (7%) gel and immunoblotting with antibodies to recombinant and native HCF. As shown in FIG. 5, panel C, the 150-, 120-, and 110-kD proteins were present, suggesting that these species are generated in vivo. The 300-kD protein was not apparent in the whole-cell extracts.

CO-IMMUNE PRECIPITATION OF VP16 AND HCF POLYPEPTIDES FROM HELA EXTRACTS

The observations that HCF facilitates complex formation between VP16, Oct-1, and TAATGARAT and binds to a VP16 affinity column suggest that HCF and VP16 interact directly in vitro. We next sought to ascertain whether VP16 and HCF could be co-immune precipitated from a HeLa whple cell extract. HeLa monolayers were lysed in lysis buffer, and the extracts were supplemented with GST-VP16deltaC and incubated with an antibody to VP16 (LP1; McLean et al, supra). The immune complexes were isolated with protein A—Sepharose, heated to 100° C. in SDS sample buffer, and separated by SDS PAGE. HCF polypeptides that co-immune precipitated with VP16 were visualized by immunoblotting with antiserum to rHCF. Only from the VP16-supplemented extracts could the 300-, 150-, 120-, and 110-kD forms of HCF be co-immune precipitated with the VP16 antibody. Identical membranes were immunoblotted with antisera to three other nuclear proteins (NFkB p50, TATA binding protein, and c-Jun); none of the three could be co-immune precipitated with antibody to VP16, suggesting that the VP16-HCF interaction is specific. When VP16 is delivered to HeLa cells via infection with HSV-1, the HCF polypeptides could also be co-immune precipitated with the VP16 antibody.

DISCUSSION

HCF activity is necessary for allowing stable interaction of VP16,Oct1, and the HSV IE gene regulatory element TAATGARAT in vitro. Because VP16 carries out its transcriptional activation function only when tethered to DNA, the presence of HCF appears crucial for activation of HSV IE genes in vivo. When EMSAs are performed there is no apparent Oct-1-HCF-DNA complex; this, along with the the observation that HCF binds to a VP16 affinity column in the absence of Oct-1 suggests that HCF interacts directly with VP16, but not with Oct1, at least not in the absence of VP16. One possibility is that HCF interacts with VP16 and renders it competant to bind to Oct-1. The complex then in turn can contact IE gene regulatory sequences.

HCF activity consists of a collection of polypeptides of 110, 120, 150, and 300 kD encoded by a single structural gene that gives rise to a parent protein of 2039 amino acids. This parent protein appears to be processed in vivo to yield multiple immunologically related forms of HCF that correspond in molecular weight to the polypeptides we observed during purification of HCF activity. The deduced amino acid sequence of the full-length HCF clone contains 6 threonine-rich repeats that are potential sites of phosphorylation. These repeated motifs are positioned such that proteolytic processing within the repeats generates proteins of the sizes we observed in purified HCF fractions. Thus, the regulated processing at the repeats is responsible for generating various components of HCF activity.

HCF allows formation of a stable HCF-VP16-Oct-1-TAATGARAT complex in vitro. However, HCF is shown to be present in a number of mammalian cell lines and is conserved throughout evolution from insects to humans. During fractionation HCF polypeptides appear in multiple fractions on a number of diverse columns, rather than as a distinct peak of activity. This indicates that HCF interacts with a variety of nuclear proteins and participates in the assembly of multiple protein-DNA regulatory complexes in vivo.

Use of HCF in drug screening assays.

Coming ELISA strip wells (8 wells per strip) were coated with avidin (1.0 ug per well) by incubating avidin (200 ul of a 5 ug/ml stock) in coupling buffer (per liter: 1.6 g $Na_2CO_3$, 2.9 g, $NaHCO_3$, 0.9 g $NAN_3$) on the well for 12 h at 4° C. The buffer was decanted, and nonspecific binding sites on the wells were blocked with 1% skim milk in phosphate-buffered saline (PBS) for 1 h at 37° C. Blocking buffer was discarded, and the TAATGARAT-containing oligonucleotide (1 pmol/well) was added to the wells and incubated for 30 min at room temperature. The oligonucleotide was double-stranded and contained a biotin tag on the sense strand.

The oligo-containing solution was then removed, and the wells were washed with 1% milk in PBS. VP16 engineered to contain the heart muscle kinase phosphorylation site (HMK-VP16) was labeled with $\gamma^{32}$P-ATP and mixed with recombinant Oct1-POU domain and partially purified HCF, all in HEG buffer (0.1M KCl, 25 mM HEPES pH 7.9, 0.5 mM EDTA, 20% glycerol, 0.01% LDAO, 0.1M AEBSF, 0.1M Na metabisulfite, 10 mM β-mercaptoethanol) plus 200 ug/ml bovine serum albumin (BSA).

The protein mixture was then added to the prepared wells and incubated for 30 min at room temperature. Samples were then removed, and the wells were washed three times with the PBS/milk solution. Wells were separated and put into scintillation vials, scintillation cocktail was added, and samples were counted in a liquid scintillation counter.

Binding of VP16 to the wells was found to be dependent on the presence of Oct1, HCF, and TAATGARAT-containing oligonucleotide. Small molecules are introduced into the assay, and those that inhibit binding of $^{32}$P-VP16 purified, characterized and applied diagnostically and therapuetically as disclosed herein.

It is evident from the above results that one can use the methods and compositions disclosed herein for making and identifying diagnostic probes and therapeutic drugs. VP16 is a viral transcriptional activation protein that on its own is not a site-specific DNA binding protein but rather requires the HCF, to be recruited to the DNA. In addition to Herpes Simplex Virus, several other human viral pathogens such as Adenovirus, Herpes Zoster Virus, Cytomegolavirus, Ebstein-Barr Virus and Hepatitis B Virus have transactivator proteins that, like VP16, are not by themselves site-specific DNA binding proteins. Occupying a central role in the recruitment of viral transactivators to DNA, HCF provides a key ingredient in the identification, design, and production of useful drugs against these human pathogens.

It will also be clear to one skilled in the art from a reading of this disclosure that advantage can be taken to effect alterations of gene expression: both genes encoding HCF and genes amenable to HCF-mediated transcriptional modulation, especially viral genes. Such alterations can be effected for example, using a variety of gene therapy protocols.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

A T G C T A A T G A   R A T                 1 3

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GAGAACCAGT GGTTTGATGT GGGCGTGATC AAG                    33

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAGCAGGAGC TNCAGCCTGG CACAGCCTAC AAG                    33

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

ATGCTAATGA TAT          13

( 2 ) INFORMATION FOR SEQ ID NO:5:

( i ) SEQUENCE CHARACTERISTICS:
        ( A ) LENGTH: 2035 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met Ala Ser Ala Val Ser Pro Ala Asn Leu Pro Ala Val Leu Leu Gln
 1               5                  10                  15

Pro Arg Trp Lys Arg Val Val Gly Trp Ser Gly Pro Val Pro Arg Pro
                20                  25                  30

Arg His Gly His Arg Ala Val Ala Ile Lys Glu Leu Ile Val Val Phe
                35                  40                  45

Gly Gly Gly Asn Glu Gly Ile Val Asp Glu Leu His Val Tyr Asn Thr
            50                  55                  60

Ala Thr Asn Gln Trp Phe Ile Pro Ala Val Arg Gly Asp Ile Pro Pro
65                  70                  75                  80

Gly Cys Ala Ala Tyr Gly Phe Val Cys Asp Gly Thr Arg Leu Leu Val
                85                  90                  95

Phe Gly Gly Met Val Glu Tyr Gly Lys Tyr Ser Asn Asp Leu Tyr Glu
                100                 105                 110

Leu Gln Ala Ser Arg Trp Glu Trp Lys Arg Leu Lys Ala Lys Thr Pro
            115                 120                 125

Lys Asn Gly Pro Pro Pro Cys Pro Arg Leu Gly His Ser Phe Ser Leu
        130                 135                 140
```

-continued

| | | | | | | | | | | | | | | | |
|---|---|---|---|---|---|---|---|---|---|---|---|---|---|---|---|
| Val | Gly | Asn | Lys | Cys | Tyr | Leu | Phe | Gly | Gly | Leu | Ala | Asn | Asp | Ser | Glu |
| 145 | | | | | 150 | | | | | 155 | | | | | 160 |
| Asp | Pro | Lys | Asn | Asn | Ile | Pro | Arg | Tyr | Leu | Asn | Asp | Leu | Tyr | Ile | Leu |
| | | | | 165 | | | | 170 | | | | | 175 | | |
| Glu | Leu | Arg | Pro | Gly | Ser | Gly | Val | Val | Ala | Trp | Asp | Ile | Pro | Ile | Thr |
| | | | 180 | | | | | 185 | | | | | 190 | | |
| Tyr | Gly | Val | Leu | Pro | Pro | Pro | Arg | Glu | Ser | His | Thr | Ala | Val | Val | Tyr |
| | | 195 | | | | | 200 | | | | | 205 | | | |
| Thr | Glu | Lys | Asp | Asn | Lys | Lys | Ser | Lys | Leu | Val | Ile | Tyr | Gly | Gly | Met |
| | 210 | | | | | 215 | | | | | 220 | | | | |
| Ser | Gly | Cys | Arg | Leu | Gly | Asp | Leu | Trp | Thr | Leu | Asp | Ile | Asp | Thr | Leu |
| 225 | | | | | 230 | | | | | 235 | | | | | 240 |
| Thr | Trp | Asn | Lys | Pro | Ser | Leu | Ser | Gly | Val | Ala | Pro | Leu | Pro | Arg | Ser |
| | | | | 245 | | | | | 250 | | | | | 255 | |
| Leu | His | Ser | Ala | Thr | Thr | Ile | Gly | Asn | Lys | Met | Tyr | Val | Phe | Gly | Gly |
| | | | | 260 | | | | 265 | | | | | 270 | | |
| Trp | Val | Pro | Leu | Val | Met | Asp | Asp | Val | Lys | Val | Ala | Thr | His | Glu | Lys |
| | | 275 | | | | | 280 | | | | | 285 | | | |
| Glu | Trp | Lys | Cys | Thr | Asn | Thr | Leu | Ala | Cys | Leu | Asn | Leu | Asp | Thr | Met |
| | 290 | | | | | 295 | | | | | 300 | | | | |
| Ala | Trp | Glu | Thr | Ile | Leu | Met | Asp | Thr | Leu | Glu | Asp | Asn | Ile | Pro | Arg |
| 305 | | | | | 310 | | | | | 315 | | | | | 320 |

| | | | | | | | | | | | | | | | |
|---|---|---|---|---|---|---|---|---|---|---|---|---|---|---|---|
| Ala | Arg | Ala | Gly | His | Cys | Ala | Val | Ala | Ile | Asn | Thr | Arg | Leu | Tyr | Ile |
| | | | | 325 | | | | | 330 | | | | | 335 | |
| Trp | Ser | Gly | Arg | Asp | Gly | Tyr | Arg | Lys | Ala | Trp | Asn | Asn | Gln | Val | Cys |
| | | | 340 | | | | | 345 | | | | | 350 | | |
| Cys | Lys | Asp | Leu | Trp | Tyr | Leu | Glu | Thr | Glu | Lys | Pro | Pro | Pro | Pro | Ala |
| | | 355 | | | | | 360 | | | | | 365 | | | |
| Arg | Val | Gln | Leu | Val | Arg | Ala | Asn | Thr | Asn | Ser | Leu | Glu | Val | Ser | Trp |
| | 370 | | | | | 375 | | | | | 380 | | | | |
| Gly | Ala | Val | Ala | Thr | Ala | Asp | Ser | Tyr | Leu | Leu | Gln | Leu | Gln | Lys | Tyr |
| 385 | | | | | 390 | | | | | 395 | | | | | 400 |
| Asp | Ile | Pro | Ala | Thr | Ala | Ala | Thr | Ala | Thr | Ser | Pro | Thr | Pro | Asn | Pro |
| | | | | 405 | | | | | 410 | | | | | 415 | |
| Val | Pro | Ser | Val | Pro | Ala | Asn | Pro | Pro | Lys | Ser | Pro | Ala | Pro | Ala | Ala |
| | | | 420 | | | | | 425 | | | | | 430 | | |
| Ala | Ala | Pro | Ala | Val | Gln | Pro | Leu | Thr | Gln | Val | Gly | Ile | Thr | Leu | Leu |
| | | | 435 | | | | | 440 | | | | | 445 | | |
| Pro | Gln | Ala | Ala | Pro | Ala | Pro | Pro | Thr | Thr | Thr | Thr | Ile | Gln | Val | Leu |
| | 450 | | | | | 455 | | | | | 460 | | | | |
| Pro | Thr | Val | Pro | Gly | Ser | Ser | Ile | Ser | Val | Pro | Thr | Ala | Ala | Arg | Thr |
| 465 | | | | | 470 | | | | | 475 | | | | | 480 |
| Gln | Gly | Val | Pro | Ala | Val | Leu | Lys | Val | Thr | Gly | Pro | Gln | Ala | Thr | Thr |
| | | | | 485 | | | | | 490 | | | | | 495 | |
| Gly | Thr | Pro | Leu | Val | Thr | Met | Arg | Pro | Ala | Ser | Gln | Ala | Gly | Lys | Ala |
| | | | 500 | | | | | 505 | | | | | 510 | | |
| Pro | Val | Thr | Val | Thr | Ser | Leu | Pro | Ala | Gly | Val | Arg | Met | Val | Val | Pro |
| | | | 515 | | | | | 520 | | | | | 525 | | |
| Thr | Gln | Ser | Ala | Gln | Gly | Thr | Val | Ile | Gly | Ser | Ser | Pro | Gln | Met | Ser |

|     |     |     | 530 |     |     |     | 535 |     |     |     | 540 |     |     |     |
| --- | --- | --- | --- | --- | --- | --- | --- | --- | --- | --- | --- | --- | --- | --- |
| Gly 545 | Met | Ala | Ala | Leu 550 | Ala | Ala | Ala | Ala 555 | Ala | Thr | Gln | Lys | Ile | Pro 560 |
| Pro | Ser | Ser | Ala | Pro 565 | Thr | Val | Leu | Ser 570 | Val | Pro | Ala | Gly | Thr 575 | Ile |
| Val | Lys | Thr | Met 580 | Ala | Val | Thr | Pro | Gly 585 | Thr | Thr | Thr | Leu | Pro 590 | Ala | Thr |

—

| Val | Lys | Val 595 | Ala | Ser | Ser | Pro | Val 600 | Met | Val | Ser | Asn | Pro 605 | Ala | Thr | Arg |
| --- | --- | --- | --- | --- | --- | --- | --- | --- | --- | --- | --- | --- | --- | --- | --- |
| Met | Leu 610 | Lys | Thr | Ala | Ala | Ala 615 | Gln | Val | Gly | Thr | Ser 620 | Val | Ser | Ser | Ala |
| Thr 625 | Asn | Thr | Ser | Thr | Arg 630 | Pro | Ile | Ile | Thr | Val 635 | His | Lys | Ser | Gly | Thr 640 |
| Val | Thr | Val | Ala | Gln 645 | Gln | Ala | Gln | Val | Val 650 | Thr | Thr | Val | Val | Gly 655 | Gly |
| Val | Thr | Lys | Thr 660 | Ile | Thr | Leu | Val | Lys 665 | Ser | Pro | Ile | Ser | Val 670 | Pro | Gly |
| Gly | Ser | Ala 675 | Leu | Ile | Ser | Asn | Leu 680 | Gly | Lys | Val | Met | Ser 685 | Val | Val | Gln |
| Thr | Lys 690 | Pro | Val | Gln | Thr | Ser 695 | Ala | Val | Thr | Gly | Gln 700 | Ala | Ser | Thr | Gly |
| Pro 705 | Val | Thr | Gln | Ile | Ile 710 | Gln | Thr | Lys | Gly | Pro 715 | Leu | Pro | Ala | Gly | Thr 720 |
| Ile | Leu | Lys | Leu | Val 725 | Thr | Ser | Ala | Asp | Gly 730 | Lys | Pro | Thr | Thr | Ile 735 | Ile |
| Thr | Thr | Thr | Gln 740 | Ala | Ser | Gly | Ala | Gly 745 | Thr | Lys | Pro | Thr | Ile 750 | Leu | Gly |
| Ile | Ser | Ser 755 | Val | Ser | Pro | Ser | Thr 760 | Thr | Lys | Pro | Gly | Thr 765 | Thr | Thr | Ile |
| Ile | Lys 770 | Thr | Ile | Pro | Met | Ser 775 | Ala | Ile | Ile | Thr | Gln 780 | Ala | Gly | Ala | Thr |
| Gly 785 | Val | Thr | Ser | Ser | Pro 790 | Gly | Ile | Lys | Ser | Pro 795 | Ile | Thr | Ile | Ile | Thr 800 |
| Thr | Lys | Val | Met | Thr 805 | Ser | Gly | Thr | Gly | Ala 810 | Pro | Ala | Lys | Ile | Ile 815 | Thr |
| Ala | Val | Pro | Lys 820 | Ile | Ala | Thr | Gly | His 825 | Gly | Gln | Gln | Gly | Val 830 | Thr | Gln |
| Val | Val | Leu 835 | Lys | Gly | Ala | Pro | Gly 840 | Gln | Pro | Gly | Thr | Ile 845 | Leu | Arg | Thr |

|     | Val | Pro | Met | Gly | Gly | Val | Arg | Leu | Val | Thr | Pro | Val | Thr | Val | Ser | Ala |
| --- | --- | --- | --- | --- | --- | --- | --- | --- | --- | --- | --- | --- | --- | --- | --- | --- |
|     |     | 850 |     |     |     |     | 855 |     |     |     |     | 860 |     |     |     |     |
|     | Val | Lys | Pro | Ala | Val | Thr | Thr | Leu | Val | Val | Lys | Gly | Thr | Thr | Gly | Val |
|     | 865 |     |     |     |     | 870 |     |     |     |     | 875 |     |     |     |     | 880 |
|     | Thr | Thr | Leu | Gly | Thr | Val | Thr | Gly | Thr | Val | Ser | Thr | Ser | Leu | Ala | Gly |

-continued

|                                                                                                                       885                                             890                                           895                        |
| --------------------------------------------------------------------------------------------------------------------------------------------------------------------------------------------------------------------------------------------- |

Ala Gly Gly His Ser Thr Ser Ala Ser Leu Ala Thr Pro Ile Thr Thr
                 900                     905                     910

Leu Gly Thr Ile Ala Thr Leu Ser Ser Gln Val Ile Asn Pro Thr Ala
        915                     920                     925

Ile Thr Val Ser Ala Ala Gln Thr Thr Leu Thr Ala Ala Gly Gly Leu
        930                     935                     940

Thr Thr Pro Thr Ile Thr Met Gln Pro Val Ser Gln Pro Thr Gln Val
945                     950                     955                     960

Thr Leu Ile Thr Ala Pro Ser Gly Val Glu Ala Gln Pro Val His Asp
                965                     970                     975

Leu Pro Val Ser Ile Leu Ala Ser Pro Thr Thr Glu Gln Pro Thr Ala
                980                     985                     990

Thr Val Thr Ile Ala Asp Ser Gly Gln Gly Asp Val Gln Pro Gly Thr
                995                     1000                    1005

Val Thr Leu Val Cys Ser Asn Pro Pro Cys Glu Thr His Glu Thr Gly
        1010                    1015                    1020

Thr Thr Asn Thr Ala Thr Thr Thr Val Val Ala Asn Leu Gly Gly His
1025                    1030                    1035                    1040

Pro Gln Pro Thr Gln Val Gln Phe Val Cys Asp Arg Gln Glu Ala Ala
                1045                    1050                    1055

Ala Ser Leu Val Thr Ser Thr Val Gly Gln Gln Asn Gly Ser Val Val
                1060                    1065                    1070

Arg Val Cys Ser Asn Pro Pro Cys Glu Thr His Glu Thr Gly Thr Thr
        1075                    1080                    1085

Asn Thr Ala Thr Thr Ala Thr Ser Asn Met Ala Gly Gln His Gly Cys
        1090                    1095                    1100

Ser Asn Pro Pro Cys Glu Thr His Glu Thr Gly Thr Thr Asn Thr Ala
1105                    1110                    1115                    1120

|                                                                                                                                                                                                                                              |
| --------------------------------------------------------------------------------------------------------------------------------------------------------------------------------------------------------------------------------------------- |

Thr Thr Ala Met Ser Ser Val Gly Ala Asn His Gln Arg Asp Ala Arg
        1125                    1130                    1135

Arg Ala Cys Ala Ala Gly Thr Pro Ala Val Ile Arg Ile Ser Val Ala
        1140                    1145                    1150

Thr Gly Ala Leu Glu Ala Ala Gln Gly Ser Lys Ser Gln Cys Gln Thr
        1155                    1160                    1165

Arg Gln Thr Ser Ala Thr Ser Thr Thr Met Thr Val Met Ala Thr Gly
        1170                    1175                    1180

Ala Pro Cys Ser Ala Gly Pro Leu Leu Gly Pro Ser Met Ala Arg Glu
1185                    1190                    1195                    1200

Pro Gly Gly Arg Ser Pro Ala Phe Val Gln Leu Ala Pro Leu Ser Ser
                1205                    1210                    1215

Lys Val Arg Leu Ser Ser Pro Ser Ile Lys Asp Leu Pro Ala Gly Arg
                1220                    1225                    1230

His Ser His Ala Val Ser Thr Ala Ala Met Thr Arg Ser Ser Val Gly
                1235                    1240                    1245

Ala Gly Glu Pro Arg Met Ala Pro Val Cys Glu Ser Leu Gln Gly Gly
                1250                    1255                    1260

Ser Pro Ser Thr Thr Val Thr Val Thr Ala Leu Glu Ala Leu Leu Cys
1265                    1270                    1275                    1280

| | | | | | | | | | | | | | | |
|---|---|---|---|---|---|---|---|---|---|---|---|---|---|---|
|Pro|Ser|Ala|Thr|Val 1285|Thr|Gln|Val|Cys|Ser 1290|Asn|Pro|Pro|Cys|Glu Thr 1295|
|His|Glu|Thr|Gly 1300|Thr|Thr|Asn|Thr|Ala 1305|Thr|Thr|Ser|Asn|Ala 1310|Gly Ser|
|Ala|Gln|Arg 1315|Val|Cys|Ser|Asn|Pro 1320|Pro|Cys|Glu|Thr|His 1325|Glu|Thr Gly|
|Thr|Thr 1330|His|Thr|Ala|Thr|Thr 1335|Ala|Thr|Ser|Asn|Gly 1340|Gly|Thr|Gly Gln|
|Pro 1345|Glu|Gly|Gly|Gln|Gln 1350|Pro|Pro|Ala|Gly|Arg 1355|Pro|Cys|Glu|Thr His 1360|
|Gln|Thr|Thr|Ser|Thr 1365|Gly|Thr|Thr|Met|Ser 1370|Val|Ser|Val|Gly 1375|Ala Leu|

| | | | | | | | | | | | | | | |
|---|---|---|---|---|---|---|---|---|---|---|---|---|---|---|
|Leu|Pro|Asp|Ala 1380|Thr|Ser|Ser|His|Arg 1385|Thr|Val|Glu|Ser|Gly 1390|Leu Glu|
|Val|Ala|Ala 1395|Ala|Pro|Ser|Val|Thr 1400|Pro|Gln|Ala|Gly|Thr 1405|Ala|Leu Leu|
|Ala|Pro|Phe 1410|Pro|Thr|Gln|Arg|Val 1415|Cys|Ser|Asn|Pro|Pro 1420|Cys|Glu Thr|
|His|Glu|Thr|Gly|Thr 1425|Thr|His|Thr|Ala 1430|Thr|Thr|Val|Thr 1435|Ser|Asn Met 1440|
|Ser|Ser|Asn|Gln|Asp 1445|Pro|Pro|Ala|Ala 1450|Ser|Asp|Gln|Gly 1455|Glu|Val|
|Glu|Ser|Thr|Gln 1460|Gly|Asp|Ser|Val 1465|Asn|Ile|Thr|Ser|Ser 1470|Ala|Ile|
|Thr|Thr|Thr|Val 1475|Ser|Ser|Thr|Leu 1480|Thr|Arg|Ala|Val|Thr 1485|Val|Thr|
|Gln|Ser|Thr|Pro 1490|Val|Pro|Gly|Pro 1495|Ser|Val|Pro|Pro|Pro 1500|Glu|Glu Leu|
|Gln 1505|Val|Ser|Pro|Gly|Pro 1510|Arg|Gln|Gln|Leu|Pro 1515|Pro|Arg|Gln|Leu Leu 1520|
|Gln|Ser|Ala|Ser|Thr 1525|Ala|Leu|Met|Gly|Glu 1530|Ser|Ala|Glu|Val 1535|Leu Ser|
|Ala|Ser|Gln|Thr 1540|Pro|Glu|Leu|Pro|Ala 1545|Ala|Val|Asp|Leu|Ser 1550|Ser Thr|
|Gly|Glu|Pro|Ser|Ser 1555|Gly|Gln|Glu|Ser 1560|Ala|Gly|Ser|Ala|Val 1565|Val Ala|
|Thr|Val 1570|Val|Val|Gln|Pro|Pro 1575|Pro|Thr|Gln|Ser|Glu 1580|Val|Asp Gln|
|Leu|Ser 1585|Leu|Pro|Gln|Glu|Leu 1590|Met|Ala|Glu|Ala|Gln 1595|Ala|Gly|Thr Thr 1600|
|Thr|Leu|Met|Val|Thr 1605|Gly|Leu|Thr|Pro|Glu 1610|Glu|Leu|Ala|Val 1615|Thr Ala|
|Ala|Ala|Glu|Ala|Ala 1620|Ala|Gln|Ala|Ala|Ala 1625|Thr|Glu|Glu|Ala 1630|Gln Ala|

```
Leu Ala Ile Gln Ala Val Leu Gln Ala Ala Gln Gln Ala Val Met Gly
            1635                1640                1645

Thr Gly Glu Pro Met Asp Thr Ser Glu Ala Ala Ala Thr Val Thr Gln
            1650                1655                1660

Ala Glu Leu Gly His Leu Ser Ala Glu Gly Gln Glu Gly Gln Ala Thr
1665                1670                1675                1680

Thr Ile Pro Ile Val Leu Thr Gln Gln Glu Leu Ala Ala Leu Val Gln
            1685                1690                1695

Gln Gln Gln Leu Gln Glu Ala Gln Ala Gln Gln His His His Leu
            1700                1705                1710

Pro Thr Glu Ala Leu Ala Pro Ala Asp Ser Leu Asn Asp Pro Ala Ile
            1715                1720                1725

Glu Ser Asn Cys Leu Asn Glu Leu Ala Gly Thr Val Pro Ser Thr Val
        1730                1735                1740

Ala Leu Leu Pro Ser Thr Ala Thr Glu Ser Leu Ala Pro Ser Asn Thr
1745                1750                1755                1760

Phe Val Ala Pro Gln Pro Val Val Val Ala Ser Pro Ala Lys Leu Gln
            1765                1770                1775

Ala Ala Ala Thr Leu Thr Glu Val Ala Asn Gly Ile Glu Ser Leu Gly
            1780                1785                1790

Val Lys Pro Asp Leu Pro Pro Pro Ser Lys Ala Pro Met Lys Lys
            1795                1800                1805

Glu Asn Gln Trp Phe Asp Val Gly Val Ile Lys Gly Thr Asn Val Met
        1810                1815                1820

Val Thr His Tyr Phe Leu Pro Pro Asp Asp Ala Val Pro Ser Asp Asp
1825                1830                1835                1840

Asp Leu Gly Thr Val Pro Asp Tyr Asn Gln Leu Lys Lys Gln Glu Leu
            1845                1850                1855

Gln Pro Gly Thr Ala Tyr Lys Phe Arg Val Ala Gly Ile Asn Ala Cys
            1860                1865                1870

Gly Arg Gly Pro Phe Ser Glu Ile Ser Ala Phe Lys Thr Cys Leu Pro
            1875                1880                1885

Gly Phe Pro Gly Ala Pro Cys Ala Ile Lys Ile Ser Lys Ser Pro Asp
            1890                1895                1900

Gly Ala His Leu Thr Trp Glu Pro Pro Ser Val Thr Ser Gly Lys Ile
1905                1910                1915                1920

Ile Glu Tyr Ser Val Tyr Leu Ala Ile Gln Ser Ser Gln Ala Gly Gly
            1925                1930                1935

Glu Leu Lys Ser Ser Thr Pro Ala Gln Leu Ala Phe Met Arg Val Tyr
            1940                1945                1950

Cys Gly Pro Ser Pro Ser Cys Leu Val Gln Ser Ser Ser Leu Ser Asn
            1955                1960                1965

Ala His Ile Asp Tyr Thr Thr Lys Pro Ala Ile Ile Phe Arg Ile Ala
        1970                1975                1980

Ala Arg Asn Glu Lys Gly Tyr Gly Pro Ala Thr Gln Val Arg Trp Leu
1985                1990                1995                2000

Gln Glu Thr Ser Lys Asp Ser Ser Gly Thr Lys Pro Ala Asn Lys Arg
            2005                2010                2015

Pro Met Ser Ser Pro Glu Met Lys Ser Ala Pro Lys Lys Ser Lys Ala
```

```
                              2020                    2025                      2030

Asp Gly Gln
                         2035
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
   Thr Leu Val Cys Ser Asn Pro Pro Cys Glu Thr His Glu Thr Gly Thr
   1               5                   10                  15

Thr Asn Thr Ala Thr Thr Thr Val Val Ala
                   20                  25
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
   Val Arg Val Cys Ser Asn Pro Pro Cys Glu Thr His Glu Thr Gly Thr
   1               5                   10                  15

Thr Asn Thr Ala Thr Thr Ala Thr Ser Asn
                   20                  25
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
       Gln His Gly Cys Ser Asn Pro Pro Cys Glu Thr His Glu Thr Gly Thr
       1               5                   10                  15

Thr Asn Thr Ala Thr Thr Ala Met Ser Ser
                       20                  25
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Ala Ala Gln Gly Ser Lys Ser Gln Cys Gln Thr Arg Gln Thr Ser Ala
1               5                   10                  15

Thr Ser Thr Thr Met Thr Val Met Ala Thr
            20              25

( 2 ) INFORMATION FOR SEQ ID NO:10:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Thr Gln Val Cys Ser Asn Pro Pro Cys Glu Thr His Glu Thr Gly Thr
1               5                   10                  15

Thr Asn Thr Ala Thr Thr Ser Asn Ala Gly
            20              25

( 2 ) INFORMATION FOR SEQ ID NO:11:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Gln Arg Val Cys Ser Asn Pro Pro Cys Glu Thr His Glu Thr Gly Thr
1               5                   10                  15

Thr His Thr Ala Thr Thr Ala Thr Ser Asn
            20              25

( 2 ) INFORMATION FOR SEQ ID NO:12:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Gln Gln Pro Pro Ala Gly Arg Pro Cys Glu Thr His Gln Thr Thr Ser
1               5                   10                  15

Thr Gly Thr Thr Met Ser Val Ser Val Gly
            20              25

( 2 ) INFORMATION FOR SEQ ID NO:13:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Gln Arg Val Cys Ser Asn Pro Pro Cys Glu Thr His Glu Thr Gly Thr
1               5                   10                  15

Thr His Thr Ala Thr Thr Val Thr Ser Asn
            20              25

( 2 ) INFORMATION FOR SEQ ID NO:14:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Gln Arg Val Cys Ser Asn Pro Pro Cys Glu Thr His Glu Thr Gly Thr
  1               5                  10                  15
Thr Asn Thr Ala Thr Thr Ala Thr Ser Asn
                 20                  25
```

( 2 ) INFORMATION FOR SEQ ID NO:15:

( i ) SEQUENCE CHARACTERISTICS:
        ( A ) LENGTH: 8252 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
AGGCGGCTCA AGATGGCGGC TCCCAGGGCC TCCCGCCCGA GCTTGTAAGC GGGAGCGCCC      60
GGACAAGTAG TCGGGGCGAC GGGACTCAGC GGCCTCCAGC TTCTTGAGCC TAGGCGCTCG     120
ACAGTTTCGG GCGGCTCTTG CGGAGACGGG GTGAGCGAGA AGAAGGGAA  GAGCCAAAGG     180
GAAGGAGGGC AGTTAAGATG GCGGCCTCCA TGGAGTCGTC TACCGCTGTG TGAGAAACCG     240
CTTCTCCGTG AGAGCTGCCT TAGACGAAAG GGGGTGTGTG AAAGGAATTG AGGGGCTCCC     300
TTCCCGCTTG TTGACTTCTC CCCACCGCAC CCTTTCCCGG AACTATGGCT TCGGCCGTGT     360
CGCCCGCCAA CTTGCCAGCG GTGCTTCTGC AGCCCCGCTG GAAGCGAGTG GTGGGCTGGT     420
CGGGTCCGGT GCCACGGCCC CGCCACGGCC ACCGCGCCGT GGCCATCAAG GAGCTCATCG     480
TGGTGTTTGG CGGCGGCAAC GAGGGAATAG TGGACGAACT GCACGTGTAC AACACGGCAA     540
CCAACCAGTG GTTCATCCCA GCCGTGAGGG GGACATTCC  CCCTGGGTGT GCAGCCTATG     600
GCTTCGTGTG TGACGGGACT CGCCTCCTGG TGTTTGGTGG GATGGTGGAG TATGGGAAAT     660
ACAGCAATGA CCTCTACGAA CTCCAGGCGA GCCGGTGGGA GTGGAAGAGA CTCAAAGCAA     720
AGACGCCCAA AAACGGGCCC CCTCCGTGTC CTCGACTCGG GCACAGCTTC TCCCTTGTGG     780
GCAACAAATG CTACCTGTTT GGGGGTCTGG CCAATGATAG CGAGGACCCA AGAACAACA      840
TTCCAAGGTA CCTGAATGAC TTATATATCC TGGAATTACG GCCAGGCTCT GGAGTGGTAG     900
CCTGGGACAT TCCCATCACT TACGGGGTCC TACCACCACC CCGGGAGTCA CATACTGCCG     960
TGGTCTACAC CGAAAAAGAC AATAAGAAGT CCAAGCTGGT GATCTACGGC GGGATGAGTG    1020
GCTGCAGGCT GGGGGACCTG TGGACCCTAG ATATTGACAC CCTGACGTGG AATAAGCCCA    1080
GTCTCAGCGG GGTGGCGCCT CTTCCTCGCA GTCTCCACTC GGCAACCACC ATCGGAAATA    1140
AAATGTACGT GTTTGGTGGC TGGGTGCCTC TCGTCATGGA TGACGTCAAA GTGGCCACAC    1200
ACGAGAAGGA GTGGAAGTGT ACCAACACGC TGGCTTGTCT CAACCTGGAT ACCATGGCCT    1260
GGGAGACCAT CCTGATGGAT ACACTGGAGG ACAACATCCC CCGTGCTCGG GCTGGCCACT    1320
GCGCAGTCGC CATCAACACC CGCCTGTACA TTTGGAGTGG GCGTGACGGC TACCGCAAGG    1380
```

```
CCTGGAACAA CCAGGTCTGC TGCAAGGACC TCTGGTACCT AGAGACAGAA AAGCCACCAC    1440
CCCCAGCCCG AGTACAACTG GTACGCGCCA ACACCAACTC CCTGGAGGTG AGCTGGGGGG    1500
CAGTGGCAAC AGCCGACAGC TACCTTCTCC AGCTCCAGAA ATATGACATT CCTGCCACGG    1560
```

```
CTGCTACTGC CACCTCCCCT ACACCCAATC CGGTCCCATC TGTGCCTGCC AACCCTCCCA    1620
AGAGCCCTGC CCCAGCAGCA GCCGCACCTG CTGTGCAGCC GCTGACCCAA GTAGGCATCA    1680
CGCTCCTGCC CCAGGCTGCC CCCGCACCCC CGACCACCAC CACCATCCAG GTCTTGCCAA    1740
CGGTGCCTGG CAGCTCCATT TCTGTGCCCA CCGCAGCCAG GACTCAAGGT GTCCTGCTG    1800
TTCTCAAAGT GACCGGTCCT CAGGCTACAA CAGGAACTCC ATTGGTCACC ATGCGACCTG    1860
CCAGCCAGGC TGGGAAAGCC CCTGTCACCG TGACCTCCCT TCCCGCCGGA GTGCGGATGG    1920
TTGTGCCAAC ACAGAGTGCC CAGGGAACGG TGATTGGCAG TAGCCCACAG ATGAGTGGGA    1980
TGGCCGCACT GGCCGCTGCG GCCGCTGCCA CCCAGAAGAT CCCCCCTTCC TCGGCACCCA    2040
CGGTGCTGAG TGTCCCAGCG GGTACCACCA TCGTGAAGAC CATGGCTGTG ACACCTGGCA    2100
CTACCACCCT CCCAGCCACT GTGAAGGTGG CCTCCTCGCC AGTCATGGTG AGCAACCCTG    2160
CCACTCGCAT GCTGAAGACT GCAGCCGCCC AGGTGGGGAC ATCGGTTTCC TCCGCCACCA    2220
ACACGTCTAC CCGCCCTATC ATCACAGTGC ACAAGTCAGG CACTGTGACA GTGGCCCAGC    2280
AAGCCCAGGT GGTGACCACA GTTGTGGGCG GGGTCACCAA GACCATCACC CTGGTGAAGA    2340
GCCCCATCTC TGTCCCAGGA GGCAGTGCTC TGATTTCCAA TCTGGGCAAA GTGATGTCGG    2400
TGGTCCAGAC CAAACCAGTT CAGACTTCAG CAGTCACAGG CCAGGCGTCC ACGGGTCCTG    2460
TGACTCAGAT CATCCAGACC AAAGGGCCCC TGCCAGCGGG AACAATCCTG AAGCTGGTGA    2520
CCTCAGCAGA TGGCAAGCCC ACCACCATCA TCACTACCAC GCAGGCCAGT GGGGCGGGGA    2580
CCAAGCCCAC CATCCTGGGC ATCAGCAGCG TCTCCCCCAG TACCACCAAG CCCGGCACGA    2640
CCACCATCAT CAAAACCATC CCCATGTCGG CCATCATCAC CAGGCGGGC GCCACGGGTG    2700
TGACCAGCAG TCCTGGCATC AAGTCCCCCA TCACCATCAT CACCACCAAG GTGATGACTT    2760
CAGGAACTGG AGCACCTGCG AAAATCATCA CTGCTGTCCC CAAAATTGCC ACTGGCCACG    2820
GGCAGCAGGG AGTGACCCAG GTGGTGCTTA AGGGGCCCC GGGACAGCCA GGCACCATCC    2880
TCCGCACTGT GCCCATGGGG GGTGTTCGCC TGGTCACACC CGTCACCGTC TCCGCCGTCA    2940
AGCCAGCCGT CACCACGTTG GTTGTGAAAG GCACCACAGG TGTCACGACC CTAGGCACAG    3000
TGACAGGCAC CGTCTCCACC AGCCTTGCCG GGGCGGGGGG CCACAGCACT AGTGCTTCCC    3060
TGGCCACGCC CATCACCACC TTGGGCACCA TTGCCACCCT CTCAAGCCAG GTGATCAACC    3120
```

```
CCACTGCCAT CACTGTGTCG GCCGCACAGA CCACGCTGAC AGCGGCAGGC GGGCTCACAA    3180
CCCCAACCAT CACCATGCAG CCCGTGTCCC AGCCCACCCA GGTAACTCTG ATCACGGCAC    3240
CTAGTGGGGT GGAGGCCCAG CCTGTGCATG ACCTCCCTGT GTCCATTCTG GCCTCCCCGA    3300
CTACAGAACA GCCCACCGCC ACAGTTACCA TCGCCGACTC AGGCCAGGGT GATGTGCAGC    3360
```

| | | | | | |
|---|---|---|---|---|---|
| CTGGCACTGT | CACCTTGGTG | TGCTCCAACC | CACCCTGTGA | GACCCACGAG | ACTGGCACCA | 3420 |
| CCAACACGGC | CACCACTACT | GTTGTGGCTA | ACCTTGGGGG | ACACCCCCAG | CCCACCCAAG | 3480 |
| TGCAGTTCGT | CTGTGACAGA | CAGGAGGCAG | CTGCTTCTCT | TGTGACCTCG | ACTGTGGGCC | 3540 |
| AGCAGAATGG | TAGCGTGGTC | CGAGTCTGTT | CGAACCCGCC | CTGCGAGACC | CACGAGACGG | 3600 |
| GCACCACCAA | CACCGCCACC | ACCGCCACCT | CCAACATGGC | CGGGCAGCAT | GGCTGCTCAA | 3660 |
| ACCCACCCTG | CGAGACCCAC | GAGACGGGCA | CCACCAACAC | TGCCACTACA | GCCATGTCGA | 3720 |
| GCGTCGGCGC | CAACCACCAG | CGAGATGCCC | GTCGGGCCTG | TGCAGCTGGC | ACCCTGCCG | 3780 |
| TGATCCGGAT | CAGTGTGGCC | ACTGGGGCGC | TGGAGGCAGC | CCAGGGCTCT | AAGTCCCAGT | 3840 |
| GCCAAACCCG | CCAGACCAGC | GCGACCAGCA | CCACCATGAC | TGTGATGGCC | ACCGGGGCCC | 3900 |
| CGTGCTCGGC | CGGCCCACTC | CTTGGGCCGA | GCATGGCACG | GGAGCCCGGG | GGCCGCAGCC | 3960 |
| CTGCTTTTGT | GCAGTTGGCC | CCTCTGAGCA | GCAAAGTCAG | GCTGAGCAGC | CAAGCATTA | 4020 |
| AGGACCTTCC | TGCGGGGCGC | CACAGCCATG | CGGTCAGCAC | CGCTGCCATG | ACCCGTTCCA | 4080 |
| GCGTGGGTGC | TGGGGAGCCC | CGCATGGCAC | CTGTGTGCGA | GAGCCTCCAG | GGTGGCTCGC | 4140 |
| CCAGCACCAC | AGTGACTGTG | ACAGCCCTGG | AGGCACTGCT | GTGCCCCTCG | CCACCGTGA | 4200 |
| CCCAAGTCTG | CTCCAACCCA | CCATGTGAGA | CCCACGAGAC | AGGCACCACC | AACACCGCCA | 4260 |
| CTACCTCGAA | TGCAGGCAGC | GCCCAGAGGG | TGTGCTCCAA | CCCGCCATGC | GAGACCCACG | 4320 |
| AGACGGGCAC | CACCCACACG | GCCACCACCG | CTACTTCAAA | CGGGGGCACG | GGCCAGCCCG | 4380 |
| AGGGTGGGCA | GCAGCCCCCT | GCTGGTCGCC | CCTGTGAGAC | ACACCAGACC | ACTTCCACTG | 4440 |
| GCACCACCAT | GTCGGTCAGC | GTGGGTGCCC | TGCTTCCCGA | CGCCACTTCT | TCCCACAGGA | 4500 |
| CCGTGGAGTC | TGGCCTAGAG | GTGGCGGCGG | CACCCAGCGT | CACCCCCAG | GCTGGCACCG | 4560 |
| CGCTGCTGGC | TCCTTTCCCA | ACACAGAGGG | TGTGCTCCAA | CCCCCCTGT | GAGACCCACG | 4620 |

| | | | | | |
|---|---|---|---|---|---|
| AGACGGGCAC | CACTCACACG | GCCACCACTG | TCACTTCCAA | CATGAGTTCA | AACCAAGACC | 4680 |
| CCCCACCTGC | TGCCAGCGAT | CAGGGAGAGG | TGGAGAGCAC | CCAGGGCGAC | AGCGTGAACA | 4740 |
| TCACCAGCTC | CAGTGCCATC | ACGACAACCG | TGTCCTCCAC | ACTGACGCGG | GCTGTGACCA | 4800 |
| CCGTGACGCA | GTCCACACCG | GTCCCGGGCC | CCTCTGTGCC | GCCCCCAGAG | GAACTCCAGG | 4860 |
| TGTCGCCAGG | TCCTCGCCAG | CAGCTGCCGC | CACGGCAGCT | TCTGCAGTCG | GCTTCCACAG | 4920 |
| CCCTGATGGG | GGAGTCCGCC | GAGGTCCTGT | CAGCCTCCCA | GACCCCTGAG | CTCCCGGCCG | 4980 |
| CCGTGGATCT | GAGCAGCACA | GGGGAGCCAT | CTTCGGGCCA | GGAGTCTGCC | GGCTCTGCGG | 5040 |
| TGGTGGCCAC | TGTGGTGGTC | CAGCCACCCC | CACCCACACA | GTCCGAAGTA | GACCAGTTAT | 5100 |
| CACTTCCCCA | AGAGCTAATG | GCCGAGGCCC | AAGCTGGCAC | CACCACCCTC | ATGGTAACGG | 5160 |
| GGCTCACCCC | CGAGGAGCTG | GCAGTGACGG | CTGCTGCAGA | AGCAGCTGCC | CAGGCCGCAG | 5220 |
| CCACGGAGGA | AGCCCAGGCC | CTGGCCATCC | AGGCGGTGCT | CCAGGCCGCG | CAGCAGGCCG | 5280 |
| TCATGGGCAC | CGGCGAGCCC | ATGGACACCT | CCGAGGCAGC | AGCAACCGTG | ACTCAGGCGG | 5340 |
| AGCTGGGGCA | CCTGTCGGCC | GAGGGTCAGG | AGGGCCAGGC | CACCACCATA | CCCATTGTGC | 5400 |
| TGACACAGCA | GGAGCTGGCT | GCCCTGGTGC | AGCAGCAGCA | GCTGCAGGAG | GCCCAGGCCC | 5460 |
| AGCAGCAGCA | TCACCACCTC | CCCACTGAGG | CCCTGGCCCC | TGCCGACAGT | CTCAACGACC | 5520 |

| | | | | | |
|---|---|---|---|---|---|
| CAGCCATTGA | GAGCAATTGC | CTCAATGAGC | TGGCCGGCAC | GGTCCCCAGC | ACTGTGGCGC | 5580 |
| TGCTGCCCTC | AACGGCCACT | GAGAGCCTGG | CTCCATCCAA | CACATTTGTG | GCCCCCAGC | 5640 |
| CGGTTGTGGT | GGCCAGCCCA | GCCAAGCTGC | AGGCTGCAGC | TACCCTGACC | GAAGTGGCCA | 5700 |
| ATGGCATCGA | GTCCCTGGGT | GTGAAGCCAG | ACCTGCCGCC | CCCACCCAGC | AAAGCCCCCA | 5760 |
| TGAAGAAGGA | AAACCAGTGG | TTTGATGTGG | GAGTCATTAA | GGGCACCAAT | GTAATGGTGA | 5820 |
| CACACTATTT | CCTGCCACCA | GATGATGCTG | TCCCATCAGA | CGATGATTTG | GCACCGTCC | 5880 |
| CTGACTATAA | CCAGCTGAAG | AAGCAGGAGC | TGCAGCCAGG | CACAGCCTAT | AAGTTTCGTG | 5940 |
| TTGCCGGAAT | CAATGCCTGT | GGCCGGGGGC | CCTTCAGCGA | AATCTCAGCC | TTTAAGACGT | 6000 |
| GCCTGCCTGG | TTTCCCAGGG | GCCCCTTGTG | CCATTAAAAT | CAGCAAAAGT | CCGGATGGTG | 6060 |
| CTCACCTCAC | CTGGGAGCCA | CCCTCTGTGA | CCTCCGGCAA | GATTATCGAG | TACTCCGTGT | 6120 |
| ACCTGGCCAT | CCAGAGCTCA | CAGGCTGGGG | GCGAGCTCAA | GAGCTCCACC | CCGGCCCAGC | 6180 |
| TGGCCTTCAT | GCGGGTGTAC | TGTGGGCCCA | GCCCTCCTG | CCTGGTGCAG | TCCTCCAGCC | 6240 |

| | | | | | |
|---|---|---|---|---|---|
| TTTCCAACGC | CCACATCGAC | TACACCACCA | AGCCCGCCAT | CATCTTCCGC | ATCGCCGCCC | 6300 |
| GCAATGAGAA | GGGCTATGGC | CCGGCCACAC | AAGTGAGGTG | GCTGCAGGAA | ACCAGTAAAG | 6360 |
| ACAGCTCTGG | CACCAAGCCA | GCCAACAAGC | GGCCCATGTC | CTCTCCAGAA | ATGAAATCTG | 6420 |
| CTCCAAAGAA | ATCTAAGGCC | GATGGTCAGT | GAGAGGAAGC | TGACTAGCCC | CTGGATTCTT | 6480 |
| CTCCAGACCC | CCCTGCTTCA | GGAACACCCG | CCAGGGCCCA | CCCCTCCCAC | CCGTCCCAG | 6540 |
| CATTCGCACT | TCACCCTCGC | GAGCCGCTGT | TCACTCCTCT | CCCCTTTCTC | TTTCTCTCTG | 6600 |
| TTTTTAAAAT | AATCTAAAGA | AAGCACATTT | TACCATTGCT | GTTGGGAGGA | AGCAGAGGCA | 6660 |
| GATGGGAAAG | CAGAGAGAGG | AGCGCGCTTC | CTTTCCTCCC | CGCTGCCGCC | CACCCTGGGG | 6720 |
| AGAGACTTTT | GCGGGGAGGG | AAGGCGGAGC | TGAGGACAGC | CAGCTCCGCC | CTCCCAAGGC | 6780 |
| TGTGCGTTCC | TGAGGGCCAG | GTCGGGGGCA | GGCATGGAGG | GGAGGAAAGG | CGTCCTCTT | 6840 |
| GGCCCTCCCC | AGAGTGGCTT | TCCTGGCACC | CTGGCCTGGG | TGTCTGGTTC | TGTTTTCTTT | 6900 |
| TCTTCCCCTT | GTGTTTCCAG | TCACCTAACT | TCCCTTCCTC | AGGCTCCCCC | GGCCCACCCT | 6960 |
| GCTCAGTGAC | CCCACAGGAA | GCTTACACAT | TTTCTCAGAG | GCCTTTGTGC | TCCCACCTCT | 7020 |
| TCTACCCTCC | CCCTCTTCTT | TCCCATTTTA | AAAAGAAAA | GAAGGAAAAA | GAAAAAGGG | 7080 |
| GCAAGGAGCC | CCGCGGCGGC | CTGGGCAGCG | CCTGTGCAGA | CCTCCCTGCA | GGCCGCACTG | 7140 |
| CCAACTGCTG | CATTTGTTGT | GTTTTTAGG | TTGCAATTGG | TGAAGTTCAC | ACTTTCATTG | 7200 |
| TAATTTTAGC | GTGTGGGGTT | TTGTCCCTTT | TTTGTTGTTG | TTAGCTGTGT | ACAGAATGTG | 7260 |
| TAACCTTTTT | TCTTTTCTCT | TTTTTTGTT | TTGTTTGTT | TTGTTTTGTT | TTTTACTTT | 7320 |
| TTTCTTCTTG | GCTAATTCTT | GGCAGGGATC | TTTCTGGAGG | AAAAGCTGGG | GCCAGCCAGG | 7380 |
| GCAGGAGAGG | TGTGAAATCT | GCCACGAGGG | GCCTGCTGTT | TGCCACCCAG | CCCAACTTCC | 7440 |
| TGTTGCTGGC | CCCTGCCCTC | TGCCCTTTTG | CCTGTCCTCA | GGCCGCTGGA | ACAAAGGAAG | 7500 |
| GACAGCTCAT | TCCTCATGGG | CGATCACTCC | GCATCTATAG | GGTCGAGCCT | AGGGGAGCTT | 7560 |

| | | | | | | |
|---|---|---|---|---|---|---|
| GAGGGAGGGC | TGGGGCCTCC | TTGTCCTGGA | TTTCCAGCTC | TCCCCATCCC | CCCTCCCTGA | 7620 |
| GCACCACCGG | CACCGCCTCC | CAAACAGGGC | TGCTGGTTTC | CGCAGCCACT | GCTCCACCTC | 7680 |
| CCCCAAATCG | TCATGGAAAG | GGTGGAGATG | GAGGGAACC | AGGCGTCCTT | GGAGGCAGCT | 7740 |
| TGGGAGGGTG | ACTGTGTAGT | GTCACCCACA | AGGGAGGCTA | GGGCAATGGA | GCAGGCCACC | 7800 |
| AGCAGCAGCT | GTGCAGCATG | GAACTCAGGC | CAGGCTCCGA | GGCTGGGGGA | TCTGCTTGGA | 7860 |
| GTTTCTGCC | CCCCACCCCA | AACTTCTGTC | GAGGAGCAAG | GCTTGCCAGC | AAGTCAGAAG | 7920 |
| GATTTGAACC | GAGCAGCCAA | TCTTTCCAGC | CCTCCCTAC | CGACCTCTGC | CTGGAGACGC | 7980 |
| AGCAGCCTGT | GTCCTCCAGG | GCCTCTGGTT | TGTTGTATTA | TAGTATATTT | CGCTGTGGAA | 8040 |
| AATGTCACGT | TTAGTCACCT | TGGAGCCCAC | TCACCTGGTC | CTGTTGTTTT | ACCCCATCCC | 8100 |
| TTCTCTCGCG | CGCCTATTGA | TTTGTTTCTG | AGGAGAGTAC | ACCGTTCACT | ATTGTAGAGT | 8160 |
| AACCCCTGTG | ACTCAATATT | ACCATAGTGC | GATGTCGTTT | TGTGCTATTT | TGAACAATTA | 8220 |
| AAAGACTTTT | TTTGAAATAA | AAAAAAAAA | AA | | | 8252 |

What is claimed is:

1. An isolated nucleic acid encoding Host Cell Factor, said Host Cell Factor having the amino acid sequence set forth as SEQ ID NO: 5.

2. A vector comprising the nucleic acid sequence of claim 1 operably linked to a transcription regulatory element not naturally linked to said nucleic acid.

3. A cell comprising a nucleic acid according to claim 1 operably linked to a transcription regulatory element not naturally linked to said nucleic acid.

4. A process for the production of a recombinant Host Cell Factor, said process comprising culturing a cell according to claim 3 under conditions suitable for the expression of said nucleic acid, and recovering said Host Cell Factor.

* * * * *